(12) United States Patent
Vogelbacher et al.

(10) Patent No.: US 8,501,748 B2
(45) Date of Patent: Aug. 6, 2013

(54) METHOD FOR THE PRODUCTION OF β-KETONITRILES

(75) Inventors: Uwe Josef Vogelbacher, Ludwigshafen (DE); Peter Otto, Ludwigshafen (DE); Michael Rack, Eppelheim (DE)

(73) Assignee: BASF SE (DE)

( * ) Notice: Subject to any disclaimer, the term of this patent is extended or adjusted under 35 U.S.C. 154(b) by 0 days.

(21) Appl. No.: 13/616,883

(22) Filed: Sep. 14, 2012

(65) Prior Publication Data

US 2013/0005970 A1   Jan. 3, 2013

Related U.S. Application Data

(62) Division of application No. 12/528,700, filed as application No. PCT/EP2008/052514 on Feb. 29, 2008, now Pat. No. 8,309,751.

(30) Foreign Application Priority Data

Mar. 2, 2007 (EP) ..................................... 07103412

(51) Int. Cl.
 *C07D 487/00* (2006.01)
(52) U.S. Cl.
 USPC ........................................................ 514/256
(58) Field of Classification Search
 None
 See application file for complete search history.

(56) References Cited

U.S. PATENT DOCUMENTS

| | | | |
|---|---|---|---|
| 4,617,303 | A | 10/1986 | Eicken et al. |
| RE32,676 | E | 5/1988 | Eicken et al. |
| 2003/0105349 | A1 | 6/2003 | Koch |
| 2004/0171863 | A1 | 9/2004 | Matsushita et al. |
| 2008/0262000 | A1 | 10/2008 | Schafer et al. |

FOREIGN PATENT DOCUMENTS

| | | |
|---|---|---|
| EP | 0 141 317 | 5/1985 |
| WO | WO 2006/087325 | 8/2006 |
| WO | WO 2006/092412 | 9/2006 |
| WO | WO 2007/099317 | 9/2007 |

OTHER PUBLICATIONS

Dorwald, F. Z., Side Reactions in Organic Synthesis, 2005, Wiley: VCH, Weinheim p. IX of Preface.
Fleming, Fraser F. et al.,"ω-Halonitriles: Domino Cyclizations to Oxa- and Carbocyclic Nitriles", J. Org. Chem., 2003, p. 3943-3946, vol. 68.
Haworth, Robert D., et al., "The constituents of Guaiacum Resin. Part II. Synthesis of di-guaiaretic Acid Dimethyl Ether", Journal of the Chemical Society, 1934, p. 1423-1429.
Ji, Yaohui et al., "A high-yielding Preparation β-Ketonitriles", Organic Letters, 2006, p. 1161-1163, vol. 8, No. 6.
International Search Report completed Jun. 6, 2008, in International Application No. PCT/EP2008/052514, filed Feb. 29, 2008.
International Preliminary Report on Patentability dated Jun. 22, 2009, from corresponding International Application No. PCT/EP2008/052514, filed Feb. 29, 2008.

*Primary Examiner* — Jeffrey Murray
(74) *Attorney, Agent, or Firm* — Brinks Hofer Gilson and Lione

(57) ABSTRACT

The present invention relates to a process for preparing β-ketonitriles of the general formula I

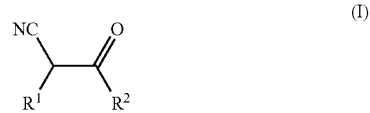

in which
R$^1$ is, inter alia, C$_1$-C$_{12}$-alkyl, C$_2$-C$_{12}$-alkenyl, C$_2$-C$_{12}$-alkinyl, C$_3$-C$_8$-cycloalkyl, C$_3$-C$_8$-cycloalkyl-C$_1$-C$_4$-alkyl, phenyl-C$_1$-C$_4$-alkyl, phenoxy-C$_1$-C$_4$-alkyl or benzyloxy-C$_1$-C$_4$-alkyl;
R$^2$ is, inter alia, hydrogen, C$_1$-C$_{12}$-alkyl, C$_2$-C$_{12}$-alkenyl, C$_2$-C$_{12}$-alkinyl, C$_3$-C$_8$-cycloalkyl, C$_3$-C$_8$-cycloalkyl-C$_1$-C$_4$-alkyl, phenyl, phenyl-C$_1$-C$_4$-alkyl, phenoxy-C$_1$-C$_4$-alkyl or benzyloxy-C$_1$-C$_4$-alkyl,
which comprises reacting a nitrile of the formula II

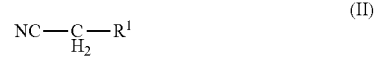

in which R$^1$ has one of the meanings given above with a carboxylic ester of the formula III

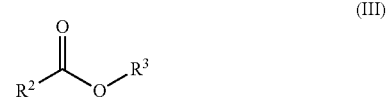

in which R$^2$ has one of the meanings given above and R$^3$ is C$_1$-C$_{12}$-alkyl, C$_1$-C$_4$-alkoxy-C$_1$-C$_4$-alkyl, C$_3$-C$_8$-cycloalkyl, C$_3$-C$_8$-cycloalkyl-C$_1$-C$_4$-alkyl, phenyl-C$_1$-C$_4$-alkyl, phenoxy-C$_1$-C$_4$-alkyl or benzyloxy-C$_1$-C$_4$-alkyl,
where the reaction is carried out in the presence of a potassium alkoxide and at least 80% of the nitrile of the formula II are added to the reaction under reaction conditions.

2 Claims, No Drawings

METHOD FOR THE PRODUCTION OF β-KETONITRILES

This application is a divisional of U.S. application Ser. No. 12/528,700, filed Aug. 26, 2009, which application is a National Stage application of International Application No. PCT/EP2008/052514 filed Feb. 29, 2008, the entire contents of which are hereby incorporated herein by reference. This application also claims the benefit under 35 U.S.C. §119 of European Patent Application No. 07103412.8, filed Mar. 2, 2007, the entire contents of which is hereby incorporated herein by reference.

The present invention relates to a process for preparing β-ketonitriles of the general formula I

in which

R$^1$ is C$_1$-C$_{12}$-alkyl, C$_2$-C$_{12}$-alkenyl, C$_2$-C$_{12}$-alkinyl, C$_3$-C$_8$-cycloalkyl, C$_3$-C$_8$-cycloalkyl-C$_1$-C$_4$-alkyl, phenyl-C$_1$-C$_4$-alkyl, phenoxy-C$_1$-C$_4$-alkyl or benzyloxy-C$_1$-C$_4$-alkyl, where C$_1$-C$_{12}$-alkyl may be substituted by one of the radicals R$^A$, the C$_3$-C$_8$-cycloalkyl groups in the radicals mentioned above may be substituted by 1, 2, 3, 4 or 5 radicals R$^B$ and the phenyl groups in the radicals mentioned above may be substituted by 1, 2, 3, 4 or 5 radicals R$^C$;

R$^A$ is selected from the group consisting of C$_1$-C$_{10}$-alkoxy, C$_1$-C$_6$-alkoxy-C$_1$-C$_4$-alkoxy, C$_1$-C$_{10}$-alkylthio, NH$_2$, C$_1$-C$_{10}$-alkylamino and di-C$_1$-C$_{10}$-alkylamino;

R$^B$ is selected from the group consisting of fluorine, C$_1$-C$_4$-alkyl, C$_1$-C$_4$-perfluoroalkyl and the meanings given for R$^A$;

R$^C$ is selected from the group consisting of fluorine, nitro, C$_1$-C$_4$-alkyl, C$_1$-C$_4$-perfluoralkyl and the meanings given for R$^A$;

R$^2$ is hydrogen, C$_1$-C$_{12}$-alkyl, C$_2$-C$_{12}$-alkenyl, C$_2$-C$_{12}$-alkinyl, C$_3$-C$_8$-cycloalkyl, C$_3$-C$_8$-cycloalkyl-C$_1$-C$_4$-alkyl, phenyl, phenyl-C$_1$-C$_4$-alkyl, phenoxy-C$_1$-C$_4$-alkyl or benzyloxy-C$_1$-C$_4$-alkyl, where C$_1$-C$_{12}$-alkyl may be substituted by one of the radicals R$^A$, the C$_3$-C$_8$-cycloalkyl groups in the radicals mentioned above may be substituted by 1, 2, 3, 4 or 5 radicals R$^B$ and the phenyl groups in the radicals mentioned above may be substituted by 1, 2, 3, 4 or 5 radicals R$^C$.

β-Ketonitriles, in particular those of the general formula I, are interesting starting materials for the preparation of heterocyclic active compounds, in particular for the preparation of fungicidally active 7-aminoazolopyrimidines (see, for example, EP-A-141317, WO2006/087325).

β-Ketonitriles are usually prepared by condensation of nitriles having hydrogen atoms in the α-position to the nitrile group with carboxylic esters in the presence of a base. In scheme 1 below, this reaction is shown for the preparation of the β-ketonitriles of the formula I. In scheme 1, the variables R$^1$ and R$^2$ have the meanings mentioned above. R is an inert radical which is attached via a carbon atom and generally has 1 to 12 carbon atoms.

Scheme 1:

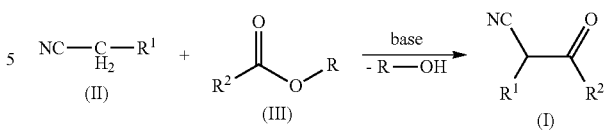

Thus, for example, EP 141317 describes the preparation of β-acylated alkyl cyanides by reacting alkyl cyanides with carboxylic esters and strong bases, for example alkali metal hydrides, alkali metal amides and metal alkyls. However, such bases are relatively expensive and difficult to handle, making it difficult to transfer this reaction to an industrial scale.

US2004/0171863, for its part, describes the preparation of β-ketonitriles by reacting a carboxylic ester with an alkylnitrile which carries two hydrogen atoms in the α-position and a base at temperatures of from 145 to 300° C. in a closed vessel, which gives the alkali metal salt of the β-ketonitrile which is then utilized using an acid. However, the reaction conditions stated in this reference give only moderate yields, in particular for nitriles having four or more carbon atoms.

WO2006/087325, for its part, describes the reaction of decanenitrile with methyl methoxyacetate and potassium tert-butoxide in anhydrous dimethylformamide. The yields found are unsatisfactory. Moreover, applicants' investigations have shown that, when relatively high temperatures are used, there is an increased formation of byproducts which are difficult to remove.

Accordingly, it is an object of the present invention to provide a process for preparing β-ketonitriles of the general formula I which solves the problems of the prior art. In particular, the process is to permit the use of inexpensive alkoxides and to afford the desired products of the formula I in high yield and with good purities.

This object is achieved by a process which comprises reacting a nitrile of the formula II

in which R$^1$ has one of the meanings mentioned above with a carboxylic ester of the formula III

in which R$^2$ has one of the meanings mentioned above and R$^3$ is C$_1$-C$_{12}$-alkyl, C$_1$-C$_4$-alkoxy-C$_1$-C$_4$-alkyl, C$_3$-C$_8$-cycloalkyl, C$_3$-C$_8$-cycloalkyl-C$_1$-C$_4$-alkyl, phenyl-C$_1$-C$_4$-alkyl, phenoxy-C$_1$-C$_4$-alkyl or benzyloxy-C$_1$-C$_4$-alkyl, where the reaction is carried out in the presence of a potassium alkoxide and at least 80% of the nitrile of the formula II are added to the reaction under reaction conditions.

The invention therefore provides a process for preparing β-ketonitriles of the general formula I, as defined at the outset, which comprises reacting a nitrile of the general formula II with a carboxylic ester of the general formula III and which is characterized in that the reaction is carried out in the presence of a potassium alkoxide and at least 80% of the nitrile of the formula II are added to the reaction under reaction conditions.

Even when using potassium alkoxide, which is easy to handle, the process according to the invention affords β-ketonitriles in high yields and with good selectivity. The process according to the invention is in particular also suitable for preparing β-ketonitriles of the formula I in which $R^1$ has three or more carbon atoms, in particular five or more carbon atoms. Using the reaction sequence shown in Scheme 1, such β-ketonitriles can, owing to the reactive inertia of the nitrile parent compounds of the formula II, only be obtained in poor yields by the route shown in Scheme 1 and using methods of the prior art, in particular when the bases used are alkoxides.

In the definitions of the substituents $R^1$, $R^2$, $R^3$, $R^4$ and $R^5$ and $R^A$, $R^B$ and $R^C$ given in the formulae above and below, collective terms were used which are generally representative for specific organic radicals. Here, in the term $C_n$—$C_m$, the variables n and m each state the possible number of carbon atoms in the respective radical. Particular meanings are:

Alkyl, and also the alkyl moieties in alkylthio, alkylamino and dialkylamino: a straight-chain or branched hydrocarbon radical having generally one to twelve carbon atoms, or 1 to 4 carbon atoms, 1 to 6 carbon atoms or 5 to 12 carbon atoms, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and their isomers, 2-ethylhexyl, 3,5,5-trimethylhexyl, 3,5-dimethylhexyl, n-heptyl, 1-methylheptyl, 2-methylheptyl, 2-ethylheptyl, 2-propylheptyl, n-octyl, 1-methyloctyl, 2-methyloctyl, n-nonyl, 1-methylnonyl, 2-methylnonyl, n-decyl, 1-methyldecyl, n-undecyl, 1-methylundecyl and n-dodecyl.

Correspondingly, alkenyl denotes a straight-chain or branched ethylenically monounsaturated hydrocarbon radical having generally two to twelve carbon atoms, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-, 2-, 3-, 4-, 5- or 6-heptenyl, 1-, 2-, 3-, 4-, 5-, 6- or 7-octenyl, 1-, 2-, 3-, 4-, 5-, 6-, 7- or 8-nonenyl, 1-, 2-, 3-, 4-, 5-, 6-, 7-, 8- or 9-decenyl.

Alkynyl is a straight-chain or branched acetylenically unsaturated hydrocarbon radical having generally two to twelve carbon atoms, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-ethyl-1-methyl-2-propynyl, 1-, 2-, 3-, 4-, 5- or 6-heptynyl, 1-, 2-, 3-, 4-, 5-, 6- or 7-octynyl, 1-, 2-, 3-, 4-, 5-, 6-, 7- or 8-nonynyl, 1-, 2-, 3-, 4-, 5-, 6-, 7-, 8- or 9-decynyl.

Cycloalkyl is a mono- or bicyclic hydrocarbon radical having generally three to eight carbon atoms, such as cyclopropyl, cyclobutyl, cyclopentyl, cyclohexyl, cycloheptyl, cyclooctyl, bicyclo[3.3.0]octyl, bicyclo[2.2.1]heptyl and bicyclo[3.2.1]octyl.

Cycloalkyl-$C_1$-$C_4$-alkyl is an alkyl radical having one to four carbon atoms which carries a cycloalkyl radical as defined above having preferably three to eight carbon atoms.

Phenyl-$C_1$-$C_4$-alkyl is an alkyl radical having one to four carbon atoms which carries a phenyl radical, and is, for example, benzyl, 1-phenylethyl or 2-phenylethyl.

Phenoxy-$C_1$-$C_4$-alkyl is an alkyl radical having one to four carbon atoms which carries a phenoxy radical as substituent. Correspondingly, benzyloxy-$C_1$-$C_4$-alkyl denotes an alkyl radical having one to four carbon atoms which carries a benzyloxy radical.

Alkoxy is an alkyl radical having one to ten and in particular one to eight carbon atoms which is attached via oxygen, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexyloxy, 1,1-dimethylpropoxy, 1,2-dimethylpropoxy, 1-methylpentyloxy, 2-methylpentyloxy, 3-methylpentyloxy, 4-methylpentyloxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy and their isomers, 2-ethylhexyloxy, 3,5,5-trimethylhexyloxy, 3,5-dimethylhexyloxy, n-heptyloxy, 1-methylheptyloxy, 2-methylheptyloxy, 2-ethylheptyloxy, 2-propylheptyloxy, n-octyloxy, 1-methyloctyloxy, 2-methyloctyloxy, n-nonyloxy, 1-methylnonyloxy, 2-methylnonyloxy and n-decyloxy.

Correspondingly, alkylthio is a straight-chain or branched alkyl radical having generally one to ten carbon atoms which is attached via sulfur atom.

Alkylamino is a straight-chain or branched alkyl radical having one to eight carbon atoms which is attached via an NH group. Correspondingly, dialkylamino is a group $NR_2$ in which R may be identical or different and is straight-chain or branched alkyl having generally one to ten carbon atoms.

Alkoxyalkyl is an alkyl radical having generally one to four carbon atoms which carries an alkoxy radical as defined above, for example methoxymethyl, ethoxymethyl, —$CH_2OCH_2$—$C_2H_5$, —$CH_2$—$OCH(CH_3)_2$, n-butoxymethyl, —$CH_2$—$OCH(CH_3)$—$C_2H_5$, —$CH_2$—$OCH_2$—CH (CH₃)₂, —CH₂—OC(CH₃), methoxyethyl, ethoxyethyl, —(CH₂)₂OCH₂—C₂H₅, —(CH₂)₂OCH(CH₃)₂, n-butoxyethyl, —(CH₂)₂OCH(CH₃)—C₂H₅, —(CH₂)₂OCH₂—CH(CH₃)₂ or —(CH₂)₂—OC(CH₃), 1-methylbutoxymethyl, 2-methylbutoxymethyl, 3-methylbutoxymethyl, 2,2-dimethylpropoxymethyl, 1-ethylpropoxymethyl, hexyloxymethyl, 1,1-dimethylpropoxymethyl, 1,2-dimethylpropoxymethyl, 1-methylpentyloxymethyl, 2-methylpentyloxymethyl, 3-methylpentyloxymethyl, 4-methylpentyloxymethyl, 1,1-dimethylbutoxymethyl, 1,2-dimethylbutoxymethyl, 1,3-dimethylbutoxymethyl, 2,2-dimethylbutoxymethyl, 2,3-dimethylbutoxymethyl, 3,3-dimethylbutoxymethyl, 1-ethylbutoxymethyl, 2-ethylbutoxymethyl, 1,1,2-trimethylpropoxymethyl, 1,2,2-trimethylpropoxymethyl, 1-ethyl-1-methylpropoxymethyl, 1-ethyl-2-methylpropoxymethyl and their isomers, 2-ethylhexyloxymethyl, 3,5,5-trimethylhexyloxymethyl, 3,5-dimethylhexyloxymethyl, n-heptyloxymethyl, 1-methylheptyloxymethyl, 2-methylheptyloxymethyl, 2-ethylheptyloxymethyl, 2-propylheptyloxymethyl, n-octyloxymethyl, 1-methyloctyloxymethyl, 2-methyloctyloxymethyl, n-nonyloxymethyl, 1-methylnonyloxymethyl, 2-methylnonyloxymethyl, n-decyloxymethyl, 1-(1-methylbutoxy)ethyl, 1-(2-methylbutoxy)ethyl, 1-(3-methylbutoxy)ethyl, 1-(2,2-dimethylpropoxy)ethyl, 1-(1-ethylpropoxy)ethyl, 1-(hexyloxy)ethyl, 1-(1,1-dimethylpropoxy)ethyl, 1-(1,2-dimethylpropoxy)ethyl, 1-(1-methylpentyloxy)ethyl, 1-(2-methylpentyloxy)ethyl, 1-(3-methylpentyloxy)ethyl, 1-(4-methylpentyloxy)ethyl, 1-(1,1-dimethylbutoxy)ethyl, 1-(1,2-dimethylbutoxy)ethyl, 1-(3-dimethylbutoxy)ethyl, 1-(2,2-dimethylbutoxy)ethyl, 1-(2,3-dimethylbutoxy)ethyl, 1-(3,3-dimethylbutoxy)ethyl, 1-(1-ethylbutoxy)ethyl, 1-(2-ethylbutoxy)ethyl, 1-(2-ethylhexyloxy)ethyl, 1-(3,5,5-trimethylhexyloxy)ethyl, 1-(3,5-dimethylhexyloxy)ethyl, 1-(n-heptyloxy)ethyl, 1-(1-methylheptyloxy)ethyl, 1-(2-propylheptyloxy)ethyl, 1-(n-octyloxy)ethyl, 1-(1-methyloctyloxy)ethyl, 1-(2-methyloctyloxy)ethyl, 1-(n-nonyloxy)ethyl, 1-(1-methylnonyloxy)ethyl, 1-(2-methylnonyloxy)ethyl, 1-(n-decyloxy)ethyl, 2-(1-methylbutoxy)ethyl, 2-(2-methylbutoxy)ethyl, 2-(3-methylbutoxy)ethyl, 2-(2,2-dimethylpropoxy)ethyl, 2-(1-ethylpropoxy)ethyl, 2-(hexyloxy)ethyl, 2-(1,1-dimethylpropoxy)ethyl, 2-(1,2-dimethylpropoxy)ethyl, 2-(1-methylpentyloxy)ethyl, 2-(2-methylpentyloxy)ethyl, 2-(3-methylpentyloxy)ethyl, 2-(4-methylpentyloxy)ethyl, 2-(1,1-dimethylbutoxy)ethyl, 2-(1,2-dimethylbutoxy)ethyl, 2-(3-dimethylbutoxy)ethyl, 2-(2,2-dimethylbutoxy)ethyl, 2-(2,3-dimethylbutoxy)ethyl, 2-(3,3-dimethylbutoxy)ethyl, 2-(1-ethylbutoxy)ethyl, 2-(2-ethylbutoxy)ethyl, 2-(2-ethylhexyloxy)ethyl, 2-(3,5,5-trimethylhexyloxy)ethyl, 2-(3,5-dimethylhexyloxy)ethyl, 2-(n-heptyloxy)ethyl, 2-(1-methylheptyloxy)ethyl, 2-(2-propylheptyloxy)ethyl, 2-(n-octyloxy)ethyl, 2-(1-methyloctyloxy)ethyl, 2-(2-methyloctyloxy)ethyl, 2-(n-nonyloxy)ethyl, 2-(1-methylnonyloxy)ethyl, 2-(2-methylnonyloxy)ethyl and 2-(n-decyloxy)ethyl.

Alkoxyalkoxy is an alkoxy radical having generally one to four carbon atoms which carries an alkoxy radical as defined above, for example methoxymethoxy, ethoxymethoxy, —OCH₂OCH₂—C₂H₅, —OCH₂—OCH(CH₃)₂, n-butoxymethoxy, —OCH₂—OCH(CH₃)—C₂H₅, —OCH₂—OCH₂—CH(CH₃)₂, —OCH₂—OC(CH₃), methoxyethoxy, ethoxyethoxy, —O(CH₂)₂OCH₂—C₂H₅, —O(CH₂)₂OCH(CH₃)₂, n-butoxyethoxy, —O(CH₂)₂OCH(CH₃)—C₂H₅, —O(CH₂)₂OCH₂—CH(CH₃)₂ or —O(CH₂)₂—OC(CH₃), etc.

Perfluoralkyl is an alkyl radical having generally one to four carbon atoms in which the hydrogen atoms are replaced by fluorine atoms. Examples of perfluoroalkyl are in particular trifluoromethyl, pentafluoroethyl, heptafluoropropyl, etc.

According to the invention, when reacting the nitrile of the formula II with the carboxylic ester of the formula III, at least 80%, in particular at least 90%, particularly preferably at least 95% and especially the total amount of at least 99% of the nitrile of the formula II are added to the reaction under reaction conditions.

The term "under reaction conditions" is familiar to the person skilled in the art and means that in the reaction vessel or in the reaction zone in which the desired reaction is carried out, the conditions present are such that the desired reaction proceeds at a satisfactory reaction rate. In the process according to the invention, this means that in the reaction vessel or in the reaction zone in which the reaction of the nitrile II with the ester III is carried out are temperatures at which, in the presence of the potassium alkoxide, a reaction of the nitrile II with the carboxylic ester III with formation of the potassium salt of the compound I can proceed at a rate which is sufficient for the reaction.

The temperatures required for the reaction can be determined by the person skilled in the art by routine experiments and are usually at least 50° C., in particular at least 80° C. and particularly preferably at least 100° C. The reaction temperatures will generally not exceed 200° C. and are preferably in the range of from 80 to 180° C. and especially in the range of from 110 to 150° C.

The reaction pressure is of minor importance for the reaction. In general, the reaction is carried out in reactors where the pressure is equalized with the atmospheric pressure, so that the reaction is carried out at atmospheric pressure. For technical reasons, it may also be advantageous to carry out the reaction at slightly reduced pressure, for example in the range of from 0.9 bar (absolute) to atmospheric pressure, or at slightly elevated pressure, for example in the range of from atmospheric pressure to 3.0 bar (absolute).

The desired amount of nitrile can be added in one or more portions or continuously over a relatively long period of time at a constant or changing rate of addition. Frequently, the amount of nitrile added during the course of the reaction will be added over a certain period of time, generally in the range of from five minutes to one hour and in particular in the range of from ten minutes to thirty minutes.

For the process according to the invention, it has furthermore been found to be advantageous to add the major amount, in particular at least 80%, of the carboxylic ester of the formula III to the reaction under reaction conditions. According to a first preferred embodiment of the invention, at least 90% and in particular at least 95% and particularly preferably the total amount or at least 99% of the carboxylic ester of the formula III are added under reaction conditions. According to another preferred embodiment, from 1 to 20% by weight and in particular from 5 to 15% by weight of the carboxylic ester are initially charged in the reaction vessel, and the remaining amount of carboxylic ester is added under reaction conditions.

If the major amount of the carboxylic ester of the formula III is added during the course of the reaction, the addition may also be in one portion, in a plurality of portions or over a relatively long period of time continuously at a constant or changing rate of addition. Preferably, the desired amount of carboxylic ester III is added over a certain period of time which is generally from five minutes to one hour and in particular from ten minutes to thirty minutes.

The reaction of the nitrile II with the carboxylic ester III is preferably carried out in an inert solvent. Examples of suitable inert solvents are aliphatic and cycloaliphatic hydrocarbons, such as hexane, heptane, octane, cyclohexane, cycloheptane and cyclooctane, aromatic hydrocarbons, in particular alkylaromatics, such as toluene, xylenes, 1,2-, 1,3- and 1,4-dimethylbenzene and mixtures thereof, mesitylene, ethylbenzene, isopropylbenzene (cumene), 1,2-, 1,3- and 1,4-methylisopropylbenzene (cymenes) and mixtures thereof, 1,3- and 1,4-diisopropylbenzene and mixtures thereof, 1,2-, 1,3- and 1,4-diethylbenzene and mixtures thereof, furthermore dialkyl ethers and alicyclic ethers, such as di-n-propyl ether, diisopropyl ether, methyl tert-butyl ether, ethyl tert-butyl ether, ethylene glycol dimethyl ether, ethylene glycol diethyl ether, diethylene glycol dimethyl ether, triethylene glycol dimethyl ether, tetrahydrofuran, 2-methyltetrahydrofuran, dioxane and tetrahydropyran. Also suitable are mixtures of the inert solvents mentioned above.

Preferred inert solvents are the alkylaromatics mentioned above and mixtures thereof with inert solvents different therefrom, for example with aliphatic and alicyclic hydrocarbons or the ethers mentioned above. Preferably, the inert solvent comprises at least 80% by weight and in particular at least 90% by weight, based on the total amount of inert solvent, of one or more alkylaromatics or a mixture of at least one alkylaromatic with one or more aliphatic or cycloaliphatic hydrocarbons. Very particularly preferably, the inert solvent comprises at least 80% by weight and in particular at least 90% by weight of alkylaromatics, in particular xylene or mesitylene. Preferably, the solvent or solvent mixture has a boiling point in the temperature range mentioned above.

The amount of solvent is generally chosen such that the total amount of materials used (i.e. the total concentration of compounds II, III and potassium alkoxide) is in the range of from 20 to 80% by weight, in particular in the range of from 30 to 70% by weight, based on the total amount of materials used and solvents.

According to the invention, the reaction is carried out in the presence of a potassium alkoxide. Here, the potassium alkoxide serves as base. If appropriate, small amounts of other bases may also be present during the reaction. In general, at least 70% by weight, preferably at least 80% by weight and in particular at least 90% by weight of the base employed are potassium alkoxide. Suitable potassium alkoxides are in particular the potassium salts of $C_1$-$C_6$-alkanols, such as potassium methoxide, potassium ethoxide, potassium propoxide, potassium n-butoxide, potassium tert-butoxide, potassium 2-butoxide and potassium (2-methyl-2-butoxide). The potassium alkoxides can also be employed in the form of mixtures. Suitable further bases are in particular sodium salts and potassium salts of weak acids, such as sodium hydroxide and potassium hydroxide, sodium carbonate and potassium carbonate, sodium alkoxides, in particular the sodium salts of $C_1$-$C_6$-alkanoles and the like, but also sodium hydride and potassium hydride. Preferably, at least 95%, in particular at least 98%, based on the total amount of base employed, are potassium alkoxide. Small amounts of potassium hydroxide resulting from the hydrolysis of the potassium alkoxide don't generally interfere. However, preferably their proportion is not more than 3% by weight and in particular not more than 1.5% by weight, based on the total amount of base.

The amount an potassium alkoxide employed is preferably at least 0.9 mol, in particular at least 1 mol and particularly preferably at least 1.1 mol per mole of nitrile of the formula II. The amount of potassium alkoxide may also be 2.5, 3 or 4 mol or more per mole of the nitrile II since larger amounts of base generally don't have any disadvantageous effect on the reaction. Preferably, the molar ratio of potassium alkoxide to the total amount of nitrile of the formula II is in the range of from 1.1:1 to 4:1, in particular from 2:1 to 4:1.

It has furthermore been found to be advantageous for the reaction if the organic solvent employed for the reaction comprises small amounts of a $C_1$-$C_4$-alkanol. The amount of $C_1$-$C_4$-alkanol is generally not more than 50 mol % and in particular not more than mol %, and is, for example, in the range of from 1 to 50 mol % or from 1 to 20 mol %, based on the total amount of the ester of the formula III employed in the reaction. Here, it has been found to be advantageous to initially charge this amount of alkanol in the reaction vessel.

The molar ratio of nitrile of the formula II to ester of the formula III is typically in the range of from 1:3 to 1.5:1, preferably in the range of from 1:2 to 1:1 and in particular in the range of from 1:1.1 to 1:1.5.

The reaction is carried out in reaction vessels customary for this purpose which are generally provided with conventional means for mixing the reactants, for example stirrers, means for adding the reactants of the formulae II and III, means for controlling the reaction temperature and the reaction pressure and the like. The reaction can be carried out continuously or discontinuously, i.e. batch-wise, the latter being preferred.

In the customary batch-wise reaction, the reaction is usually carried out in a reaction vessel provided with means for adding the nitrile of the formula II and, if appropriate, the ester of the formula III, and with suitable means for mixing the reactants, for example stirrers. The reaction can be carried out at atmospheric pressure or at elevated pressure. In general, in the batch-wise reaction, a partial amount or the total amount of the potassium alkoxide, preferably at least 80%, based on the total amount of potassium alkoxide, is initially charged in the reaction vessel, if appropriate with a partial amount or the total amount of inert solvent and, if appropriate, a partial amount or the total amount of the ester of the formula III, if appropriate up to 20% of the nitrile of the formula II and, if appropriate, the $C_1$-$C_4$-alkanol. The mixture obtained in this manner is then heated to reaction temperature, and the addition of the remaining amount of potassium alkoxide and the remaining amount of inert solvent is then initiated. Preferably, all of the alkoxide and all of the inert solvent, if desired, are initially charged in the reactor. If a partial amount or in particular the major amount of the ester of the formula III is added under reaction conditions, the addition of III is preferably carried out in parallel to the addition of the nitrile II, i.e. the start and the end of the addition of the ester III does not differ from, or only by a few minutes, the beginning and the end of the addition of the nitrile of the formula II (frequently no more than 5 min., in particular no more than 2 min.). In particular, the addition of the nitrile II and the addition of the esters III are initiated simultaneously (<±2 min.), and also ended simultaneously (<±2 min.). In general, following the termination of the addition of the nitrile II and, if appropriate, the ester III, there is a post-reaction phase during which the reaction mixture is kept at the reaction temperature for a certain period of time. In general, this period of time is at least thirty minutes and will generally not exceed 24 hours. In particular, this in the range of from 1 to 12 hours and especially in the range of from 2 to 8 hours.

After the reaction has ended, the reaction mixture can be worked up in a customary manner and the β-ketonitrile of the formula I can be isolated, if required.

For work-up of the reaction mixture, the potassium salt initially formed of the β-ketonitrile of the general formula I and any alkoxide present will generally be neutralized. To this end, the reaction mixture is mixed with water or an aqueous acid, for example an aqueous hydrochloric acid or an aqueous sulfuric acid. Preferably, during mixing, the pH is monitored, and the pH should not be lower than a value of preferably pH=2 and in particular a value of pH=3. To this end, a procedure may be adopted, for example, where a dilute aqueous acid is introduced into the reaction mixture in an amount such that the pH of the resulting aqueous phase is in the range of from pH 2 to 9 and in particular in the range of pH 3 to 8. Alternatively, the reaction mixture may be introduced into water or into an aqueous acid, and the pH of the aqueous phase may, if required, be readjusted by addition of acid to a pH in the range of pH 2 to 9 and in particular pH 3 to 8. The organic phase now comprises the desired β-ketonitrile of the formula I, if appropriate dissolved in an organic solvent.

After drying, if appropriate, the β-ketonitrile of the formula I can be isolated in a customary manner from the organic phase, for example by distilling off the organic solvent. The β-ketonitrile that remains can then be subjected to a further purification. However, it has been found that, under the reaction conditions according to the invention, the β-ketonitrile of the formula I is obtained in a purity which is generally sufficient for further reactions. Frequently, even a removal of the organic solvent can be dispensed with.

The process according to the invention is suitable in particular for preparing β-ketonitriles of the general formula I in which $R^1$ is a substituent which carries at least four carbon atoms. In the formulae I and II, $R^1$ is in particular $C_4$-$C_{12}$-alkyl, $C_3$-$C_{12}$-alkenyl, benzyl, $C_5$-$C_8$-cycloalkyl or $C_1$-$C_{10}$-alkoxy-$C_1$-$C_6$-alkyl. Particularly preferably, $R^1$ is $C_6$-$C_{12}$-alkyl. $R^1$ is likewise preferably $C_3$-$C_{12}$-alkenyl.

In particular, the process according to the invention is suitable for preparing β-ketonitriles of the general formula I in which $R^2$ is $C_1$-$C_8$-alkyl, $CF_3$, $C_3$-$C_8$-cycloalkyl or $C_1$-$C_4$-alkoxy-$C_1$-$C_4$-alkyl. In the formulae I and III, $R^2$ is in particular $C_1$-$C_8$-alkyl and especially $C_1$-$C_4$-alkyl. According to another embodiment which is likewise preferred, $R^2$ in the formulae I and III is $C_1$-$C_6$-alkoxy-$C_1$-$C_4$-alkyl and in particular $C_1$-$C_4$-alkoxymethyl or 2-$C_1$-$C_4$-alkoxyethyl.

Examples of suitable β-ketonitriles of the formula I are the compounds of the general formula I listed in Table 1 in which $R^1$ and $R^2$ each have the meanings given in one row of the table:

TABLE 1

|  | $R^1$ | $R^2$ |
|---|---|---|
| I-1 | $CH_2$—$C_6H_5$ | $CH_3$ |
| I-2 | $CH_2CH_2CH_3$ | $CH_3$ |
| I-3 | $CH_2CH_2CH_2CH_3$ | $CH_3$ |
| I-4 | $CH_2CH_2CH_2CH_2CH_3$ | $CH_3$ |
| I-5 | $CH_2CH_2CH_2CH_2CH_2CH_3$ | $CH_3$ |
| I-6 | $CH_2CH(CH_3)CH_2CH_2CH_3$ | $CH_3$ |
| I-7 | $CH_2CH(CH_2CH_3)_2$ | $CH_3$ |
| I-8 | $CH_2CH_2CH_2CH_2CH_2CH_2CH_3$ | $CH_3$ |
| I-9 | $CH_2CH_2CH_2CH_2CH_2CH_2CH_2CH_3$ | $CH_3$ |
| I-10 | $CH_2CH_2CH_2CH_2CH_2CH_2CH_2CH_2CH_3$ | $CH_3$ |
| I-11 | $CH_2CH_2CH_2CH_2CH_2CH_2CH_2CH_2CH_2CH_3$ | $CH_3$ |
| I-12 | $CH_2CH_2CH(CH_3)CH_2C(CH_3)_3$ | $CH_3$ |
| I-13 | $CH_2CH_2C(CH_3)_2CH_2C(CH_3)_3$ | $CH_3$ |
| I-14 | $(CH_2)_3$—O—$CH_3$ | $CH_3$ |
| I-15 | $(CH_2)_3$—O—$CH_2CH_3$ | $CH_3$ |
| I-16 | $(CH_2)_3$—O—$CH_2CH_2CH_3$ | $CH_3$ |
| I-17 | $(CH_2)_3$—O—$CH_2CH_2CH_3$ | $CH_3$ |
| I-18 | $(CH_2)_3$—O—$CH_2CH_2CH_2CH_2CH_3$ | $CH_3$ |
| I-19 | $(CH_2)_3$—O—$CH_2CH_2CH_2CH_2CH_3$ | $CH_3$ |
| I-20 | $(CH_2)_3$—O—$CH_2CH_2CH_2CH_2CH_2CH_2CH_3$ | $CH_3$ |
| I-21 | $(CH_2)_3$—O—$CH_2CH_2CH_2CH_2CH_2CH_2CH_2CH_3$ | $CH_3$ |
| I-22 | $(CH_2)_3$—O—$(CH_2)_8CH_3$ | $CH_3$ |
| I-23 | $(CH_2)_3$—O—$CH(CH_3)_2$ | $CH_3$ |
| I-24 | $(CH_2)_3$—O—$C(CH_3)_3$ | $CH_3$ |
| I-25 | $(CH_2)_3$—O—$CH_2C(CH_3)_3$ | $CH_3$ |
| I-26 | $(CH_2)_3$—O—$CH(CH_3)CH_2C(CH_3)_3$ | $CH_3$ |
| I-27 | $(CH_2)_3$—O—$CH(CH_2CH_3)CH_2C(CH_3)_3$ | $CH_3$ |
| I-28 | $(CH_2)_3$—O—$CH_2CH(CH_3)CH_2CH(CH_3)_2$ | $CH_3$ |
| I-29 | $(CH_2)_3$—O—$CH_2CH(CH_2CH_3)CH_2CH_2CH_3$ | $CH_3$ |
| I-30 | $(CH_2)_3$—O—$CH_2CH_2CH(CH_3)CH_2CH(CH_3)_2$ | $CH_3$ |
| I-31 | $(CH_2)_3$—O—$CH_2CH_2CH(CH_3)CH_2C(CH_3)_3$ | $CH_3$ |
| I-32 | $(CH_2)_3$—O—$CH_2CH_2CH(CH_3)CH_2CH_2CH(CH_3)_2$ | $CH_3$ |
| I-33 | $(CH_2)_3$—O—$CH_2CH_2CH(CH_3)(CH_2)_3CH(CH_3)_2$ | $CH_3$ |
| I-34 | cyclo-$C_5H_9$ | $CH_3$ |
| I-35 | cyclo-$C_6H_{11}$ | $CH_3$ |
| I-36 | $CH_2$—$C_6H_5$ | $CF_3$ |
| I-37 | $CH_2CH_2CH_3$ | $CF_3$ |
| I-38 | $CH_2CH_2CH_2CH_3$ | $CF_3$ |
| I-39 | $CH_2CH_2CH_2CH_2CH_3$ | $CF_3$ |
| I-40 | $CH_2CH_2CH_2CH_2CH_2CH_3$ | $CF_3$ |
| I-41 | $CH_2CH(CH_3)CH_2CH_2CH_3$ | $CF_3$ |
| I-42 | $CH_2CH(CH_2CH_3)_2$ | $CF_3$ |
| I-43 | $CH_2CH_2CH_2CH_2CH_2CH_2CH_3$ | $CF_3$ |
| I-44 | $CH_2CH_2CH_2CH_2CH_2CH_2CH_2CH_3$ | $CF_3$ |
| I-45 | $CH_2CH_2CH_2CH_2CH_2CH_2CH_2CH_2CH_3$ | $CF_3$ |
| I-46 | $CH_2CH_2CH_2CH_2CH_2CH_2CH_2CH_2CH_2CH_3$ | $CF_3$ |
| I-47 | $CH_2CH_2CH(CH_3)CH_2C(CH_3)_3$ | $CF_3$ |
| I-48 | $CH_2CH_2C(CH_3)_2CH_2C(CH_3)_3$ | $CF_3$ |
| I-49 | cyclo-$C_5H_9$ | $CF_3$ |
| I-50 | cyclo-$C_6H_{11}$ | $CF_3$ |
| I-51 | $CH_2CH_2CH_2CH_3$ | $CH_2CH_3$ |
| I-52 | $CH_2CH_2CH_2CH_2CH_3$ | $CH_2CH_3$ |
| I-53 | $CH_2CH_2CH_2CH_2CH_2CH_3$ | $CH_2CH_3$ |

TABLE 1-continued

| | R¹ | R² |
|---|---|---|
| I-54 | CH₂CH(CH₃)CH₂CH₂CH₃ | CH₂CH₃ |
| I-55 | CH₂CH(CH₂CH₃)₂ | CH₂CH₃ |
| I-56 | CH₂CH₂CH₂CH₂CH₂CH₂CH₃ | CH₂CH₃ |
| I-57 | CH₂CH₂CH₂CH₂CH₂CH₂CH₂CH₃ | CH₂CH₃ |
| I-58 | CH₂CH₂CH₂CH₂CH₂CH₂CH₂CH₂CH₃ | CH₂CH₃ |
| I-59 | CH₂CH₂CH₂CH₂CH₂CH₂CH₂CH₂CH₂CH₃ | CH₂CH₃ |
| I-60 | CH₂CH₂CH(CH₃)CH₂C(CH₃)₃ | CH₂CH₃ |
| I-61 | CH₂CH₂C(CH₃)₂CH₂C(CH₃)₃ | CH₂CH₃ |
| I-62 | (CH₂)₃—O—CH₃ | CH₂CH₃ |
| I-63 | (CH₂)₃—O—CH₂CH₃ | CH₂CH₃ |
| I-64 | (CH₂)₃—O—CH₂CH₂CH₃ | CH₂CH₃ |
| I-65 | (CH₂)₃—O—CH₂CH₂CH₂CH₃ | CH₂CH₃ |
| I-66 | (CH₂)₃—O—CH₂CH₂CH₂CH₂CH₃ | CH₂CH₃ |
| I-67 | (CH₂)₃—O—CH₂CH₂CH₂CH₂CH₂CH₃ | CH₂CH₃ |
| I-68 | (CH₂)₃—O—CH₂CH₂CH₂CH₂CH₂CH₂CH₃ | CH₂CH₃ |
| I-69 | (CH₂)₃—O—CH₂CH₂CH₂CH₂CH₂CH₂CH₂CH₃ | CH₂CH₃ |
| I-70 | (CH₂)₃—O—(CH₂)₈CH₃ | CH₂CH₃ |
| I-71 | (CH₂)₃—O—CH(CH₃)₂ | CH₂CH₃ |
| I-72 | (CH₂)₃—O—C(CH₃)₃ | CH₂CH₃ |
| I-73 | (CH₂)₃—O—CH₂C(CH₃)₃ | CH₂CH₃ |
| I-74 | (CH₂)₃—O—CH(CH₃)CH₂C(CH₃)₃ | CH₂CH₃ |
| I-75 | (CH₂)₃—O—CH(CH₂CH₃)CH₂C(CH₃)₃ | CH₂CH₃ |
| I-76 | (CH₂)₃—O—CH₂CH(CH₃)CH₂CH(CH₃)₂ | CH₂CH₃ |
| I-77 | (CH₂)₃—O—CH₂CH(CH₂CH₃)CH₂CH₃ | CH₂CH₃ |
| I-78 | (CH₂)₃—O—CH₂CH₂CH(CH₃)CH₂CH(CH₃)₂ | CH₂CH₃ |
| I-79 | (CH₂)₃—O—CH₂CH₂CH(CH₃)CH₂C(CH₃)₃ | CH₂CH₃ |
| I-80 | (CH₂)₃—O—CH₂CH₂CH(CH₃)CH₂CH₂CH(CH₃)₂ | CH₂CH₃ |
| I-81 | (CH₂)₃—O—CH₂CH₂CH(CH₃)(CH₂)₃CH(CH₃)₂ | CH₂CH₃ |
| I-82 | CH₂CH₂CH₃ | CH₂CH₂CH₃ |
| I-83 | CH₂CH₂CH₂CH₃ | CH₂CH₂CH₃ |
| I-84 | CH₂CH₂CH₂CH₂CH₃ | CH₂CH₂CH₃ |
| I-85 | CH₂CH(CH₃)CH₂CH₂CH₃ | CH₂CH₂CH₃ |
| I-86 | CH₂CH(CH₂CH₃)₂ | CH₂CH₂CH₃ |
| I-87 | CH₂CH₂CH₂CH₂CH₂CH₂CH₃ | CH₂CH₂CH₃ |
| I-88 | CH₂CH₂CH₂CH₂CH₂CH₂CH₂CH₃ | CH₂CH₂CH₃ |
| I-89 | CH₂CH₂CH₂CH₂CH₂CH₂CH₂CH₂CH₃ | CH₂CH₂CH₃ |
| I-90 | CH₂CH₂CH₂CH₂CH₂CH₂CH₂CH₂CH₂CH₃ | CH₂CH₂CH₃ |
| I-91 | CH₂CH₂CH(CH₃)CH₂C(CH₃)₃ | CH₂CH₂CH₃ |
| I-92 | CH₂CH₂C(CH₃)₂CH₂C(CH₃)₃ | CH₂CH₂CH₃ |
| I-93 | CH₂—O—CH₂CH₂CH₂CH₃ | CH₂CH₂CH₃ |
| I-94 | CH₂—O—CH₂CH₂CH₂CH₃ | CH₂CH₂CH₃ |
| I-95 | CH₂—O—CH₂CH₂CH₂CH₂CH₃ | CH₂CH₂CH₃ |
| I-96 | CH₂—O—CH₂CH₂CH₂CH₂CH₂CH₃ | CH₂CH₂CH₃ |
| I-97 | CH₂—O—CH₂CH₂CH₂CH₂CH₂CH₂CH₃ | CH₂CH₂CH₃ |
| I-98 | CH₂—O—CH₂CH₂CH₂CH₂CH₂CH₂CH₂CH₂CH₃ | CH₂CH₂CH₃ |
| I-99 | CH₂—O—C(CH₃)₃ | CH₂CH₂CH₃ |
| I-100 | CH₂—O—CH₂C(CH₃)₃ | CH₂CH₂CH₃ |
| I-101 | CH₂—O—CH(CH₃)CH₂C(CH₃)₃ | CH₂CH₂CH₃ |
| I-102 | CH₂—O—CH(CH₂CH₃)CH₂C(CH₃)₃ | CH₂CH₂CH₃ |
| I-103 | CH₂—O—CH₂CH(CH₃)CH₂CH(CH₃)₂ | CH₂CH₂CH₃ |
| I-104 | CH₂—O—CH₂CH(CH₂CH₃)CH₂CH₂CH₃ | CH₂CH₂CH₃ |
| I-105 | CH₂—O—CH₂CH₂CH(CH₃)CH₂CH(CH₃)₂ | CH₂CH₂CH₃ |
| I-106 | CH₂—O—CH₂CH₂CH(CH₃)CH₂C(CH₃)₃ | CH₂CH₂CH₃ |
| I-107 | CH₂—O—CH₂CH₂CH(CH₃)CH₂CH₂CH(CH₃)₂ | CH₂CH₂CH₃ |
| I-108 | CH₂—O—CH₂CH₂CH(CH₃)(CH₂)₃CH(CH₃)₂ | CH₂CH₂CH₃ |
| I-109 | (CH₂)₂—O—CH₂CH₂CH₃ | CH₂CH₂CH₃ |
| I-110 | (CH₂)₂—O—CH₂CH₂CH₃ | CH₂CH₂CH₃ |
| I-111 | (CH₂)₂—O—CH₂CH₂CH₂CH₃ | CH₂CH₂CH₃ |
| I-112 | (CH₂)₂—O—CH₂CH₂CH₂CH₂CH₃ | CH₂CH₂CH₃ |
| I-113 | (CH₂)₂—O—CH₂CH₂CH₂CH₂CH₂CH₃ | CH₂CH₂CH₃ |
| I-114 | (CH₂)₂—O—CH₂CH₂CH₂CH₂CH₂CH₂CH₃ | CH₂CH₂CH₃ |
| I-115 | (CH₂)₂—O—(CH₂)₈CH₃ | CH₂CH₂CH₃ |
| I-116 | (CH₂)₂—O—CH(CH₃)₂ | CH₂CH₂CH₃ |
| I-117 | (CH₂)₂—O—C(CH₃)₃ | CH₂CH₂CH₃ |
| I-118 | (CH₂)₂—O—CH₂C(CH₃)₃ | CH₂CH₂CH₃ |
| I-119 | (CH₂)₂—O—CH(CH₃)CH₂C(CH₃)₃ | CH₂CH₂CH₃ |
| I-120 | (CH₂)₂—O—CH(CH₂CH₃)CH₂C(CH₃)₃ | CH₂CH₂CH₃ |
| I-121 | (CH₂)₂—O—CH₂CH(CH₃)CH₂CH(CH₃)₂ | CH₂CH₂CH₃ |
| I-122 | (CH₂)₂—O—CH₂CH(CH₂CH₃)CH₂CH₂CH₃ | CH₂CH₂CH₃ |
| I-123 | (CH₂)₂—O—CH₂CH₂CH(CH₃)CH₂CH(CH₃)₂ | CH₂CH₂CH₃ |
| I-124 | (CH₂)₂—O—CH₂CH₂CH(CH₃)CH₂C(CH₃)₃ | CH₂CH₂CH₃ |
| I-125 | (CH₂)₂—O—CH₂CH₂CH(CH₃)CH₂CH₂CH(CH₃)₂ | CH₂CH₂CH₃ |
| I-126 | (CH₂)₂—O—CH₂CH₂CH(CH₃)(CH₂)₃CH(CH₃)₂ | CH₂CH₂CH₃ |
| I-127 | (CH₂)₃—O—CH₃ | CH₂CH₂CH₃ |
| I-128 | (CH₂)₃—O—CH₂CH₃ | CH₂CH₂CH₃ |
| I-129 | (CH₂)₃—O—CH₂CH₂CH₃ | CH₂CH₂CH₃ |
| I-130 | (CH₂)₃—O—CH₂CH₂CH₂CH₃ | CH₂CH₂CH₃ |
| I-131 | (CH₂)₃—O—CH₂CH₂CH₂CH₂CH₃ | CH₂CH₂CH₃ |

TABLE 1-continued

|  | R¹ | R² |
|---|---|---|
| I-132 | (CH₂)₃—O—CH₂CH₂CH₂CH₂CH₂CH₃ | CH₂CH₂CH₃ |
| I-133 | (CH₂)₃—O—CH₂CH₂CH₂CH₂CH₂CH₂CH₃ | CH₂CH₂CH₃ |
| I-134 | (CH₂)₃—O—CH₂CH₂CH₂CH₂CH₂CH₂CH₂CH₃ | CH₂CH₂CH₃ |
| I-135 | (CH₂)₃—O—(CH₃)₈CH₃ | CH₂CH₂CH₃ |
| I-136 | (CH₂)₃—O—CH(CH₃)₂ | CH₂CH₂CH₃ |
| I-137 | (CH₂)₃—O—C(CH₃)₃ | CH₂CH₂CH₃ |
| I-138 | (CH₂)₃—O—CH₂C(CH₃)₃ | CH₂CH₂CH₃ |
| I-139 | (CH₂)₃—O—CH(CH₃)CH₂C(CH₃)₃ | CH₂CH₂CH₃ |
| I-140 | (CH₂)₃—O—CH(CH₂CH₃)CH₂C(CH₃)₃ | CH₂CH₂CH₃ |
| I-141 | (CH₂)₃—O—CH₂CH(CH₃)CH₂CH(CH₃)₂ | CH₂CH₂CH₃ |
| I-142 | (CH₂)₃—O—CH₂CH₂CH(CH₃)CH₂CH₂CH₃ | CH₂CH₂CH₃ |
| I-143 | (CH₂)₃—O—CH₂CH₂CH(CH₃)CH₂CH(CH₃)₂ | CH₂CH₂CH₃ |
| I-144 | (CH₂)₃—O—CH₂CH₂CH(CH₃)CH₂C(CH₃)₃ | CH₂CH₂CH₃ |
| I-145 | (CH₂)₃—O—CH₂CH₂CH(CH₃)CH₂CH₂CH(CH₃)₂ | CH₂CH₂CH₃ |
| I-146 | (CH₂)₃—O—CH₂CH₂CH(CH₃)(CH₂)₃CH(CH₃)₂ | CH₂CH₂CH₃ |
| I-147 | CH₂CH₂CH₃ | CH₂OCH₃ |
| I-148 | CH₂CH₂CH₂CH₃ | CH₂OCH₃ |
| I-149 | CH₂CH₂CH₂CH₂CH₃ | CH₂OCH₃ |
| I-150 | CH₂CH₂CH₂CH₂CH₂CH₃ | CH₂OCH₃ |
| I-151 | CH₂CH(CH₃)CH₂CH₂CH₃ | CH₂OCH₃ |
| I-152 | CH₂CH(CH₂CH₃)₂ | CH₂OCH₃ |
| I-153 | CH₂CH₂CH₂CH₂CH₂CH₂CH₃ | CH₂OCH₃ |
| I-154 | CH₂CH₂CH₂CH₂CH₂CH₂CH₂CH₃ | CH₂OCH₃ |
| I-155 | CH₂CH₂CH₂CH₂CH₂CH₂CH₂CH₂CH₃ | CH₂OCH₃ |
| I-156 | CH₂CH₂CH₂CH₂CH₂CH₂CH₂CH₂CH₂CH₃ | CH₂OCH₃ |
| I-157 | CH₂CH₂CH(CH₃)CH₂C(CH₃)₃ | CH₂OCH₃ |
| I-158 | CH₂CH₂C(CH₃)₂CH₂C(CH₃)₃ | CH₂OCH₃ |
| I-159 | (CH₂)₃—O—CH₃ | CH₂OCH₃ |
| I-160 | (CH₂)₃—O—CH₂CH₃ | CH₂OCH₃ |
| I-161 | (CH₂)₃—O—CH₂CH₂CH₃ | CH₂OCH₃ |
| I-162 | (CH₂)₃—O—CH₂CH₂CH₂CH₃ | CH₂OCH₃ |
| I-163 | (CH₂)₃—O—CH₂CH₂CH₂CH₂CH₃ | CH₂OCH₃ |
| I-164 | (CH₂)₃—O—CH₂CH₂CH₂CH₂CH₂CH₃ | CH₂OCH₃ |
| I-165 | (CH₂)₃—O—CH₂CH₂CH₂CH₂CH₂CH₂CH₃ | CH₂OCH₃ |
| I-166 | (CH₂)₃—O—CH₂CH₂CH₂CH₂CH₂CH₂CH₂CH₃ | CH₂OCH₃ |
| I-167 | (CH₂)₃—O—(CH₃)₈CH₃ | CH₂OCH₃ |
| I-168 | (CH₂)₃—O—CH(CH₃)₂ | CH₂OCH₃ |
| I-169 | (CH₂)₃—O—C(CH₃)₃ | CH₂OCH₃ |
| I-170 | (CH₂)₃—O—CH₂C(CH₃)₃ | CH₂OCH₃ |
| I-171 | (CH₂)₃—O—CH(CH₃)CH₂C(CH₃)₃ | CH₂OCH₃ |
| I-172 | (CH₂)₃—O—CH(CH₂CH₃)CH₂C(CH₃)₃ | CH₂OCH₃ |
| I-173 | (CH₂)₃—O—CH₂CH(CH₃)CH₂CH(CH₃)₂ | CH₂OCH₃ |
| I-174 | (CH₂)₃—O—CH₂CH(CH₂CH₃)CH₂CH₂CH₃ | CH₂OCH₃ |
| I-175 | (CH₂)₃—O—CH₂CH₂CH(CH₃)CH₂CH(CH₃)₂ | CH₂OCH₃ |
| I-176 | (CH₂)₃—O—CH₂CH₂CH(CH₃)CH₂C(CH₃)₃ | CH₂OCH₃ |
| I-177 | (CH₂)₃—O—CH₂CH₂CH(CH₃)CH₂CH₂CH(CH₃)₂ | CH₂OCH₃ |
| I-178 | (CH₂)₃—O—CH₂CH₂CH(CH₃)(CH₂)₃CH(CH₃)₂ | CH₂OCH₃ |
| I-179 | CH₃ | (CH₂)₃CH₃ |
| I-180 | CH₂CH₃ | (CH₂)₃CH₃ |
| I-181 | CH₂CH₂CH₃ | (CH₂)₃CH₃ |
| I-182 | CH₂CH₂CH₂CH₃ | (CH₂)₃CH₃ |
| I-183 | CH₂CH₂CH₂CH₂CH₃ | (CH₂)₃CH₃ |
| I-184 | CH₃ | (CH₂)₄CH₃ |
| I-185 | CH₂CH₃ | (CH₂)₄CH₃ |
| I-186 | CH₂CH₂CH₃ | (CH₂)₄CH₃ |
| I-187 | CH₂CH₂CH₂CH₃ | (CH₂)₄CH₃ |
| I-188 | CH₂CH₂CH₂CH₂CH₃ | (CH₂)₄CH₃ |
| I-189 | CH₃ | (CH₂)₅CH₃ |
| I-190 | CH₂CH₃ | (CH₂)₅CH₃ |
| I-191 | CH₂CH₂CH₃ | (CH₂)₅CH₃ |
| I-192 | CH₂CH₂CH₂CH₃ | (CH₂)₅CH₃ |
| I-193 | CH₂CH₂CH₂CH₂CH₃ | (CH₂)₅CH₃ |
| I-194 | CH₃ | (CH₂)₆CH₃ |
| I-195 | CH₂CH₃ | (CH₂)₆CH₃ |
| I-196 | CH₂CH₂CH₃ | (CH₂)₆CH₃ |
| I-197 | CH₂CH₂CH₂CH₃ | (CH₂)₆CH₃ |
| I-198 | CH₂CH₂CH₂CH₂CH₃ | (CH₂)₆CH₃ |
| I-199 | CH₃ | (CH₂)₇CH₃ |
| I-200 | CH₂CH₃ | (CH₂)₇CH₃ |
| I-201 | CH₂CH₂CH₃ | (CH₂)₇CH₃ |
| I-202 | CH₂CH₂CH₂CH₃ | (CH₂)₇CH₃ |
| I-203 | CH₂CH₂CH₂CH₂CH₃ | (CH₂)₇CH₃ |
| I-204 | CH₃ | (CH₂)₈CH₃ |
| I-205 | CH₂CH₃ | (CH₂)₈CH₃ |
| I-206 | CH₂CH₂CH₃ | (CH₂)₈CH₃ |
| I-207 | CH₂CH₂CH₂CH₃ | (CH₂)₈CH₃ |
| I-208 | CH₂CH₂CH₂CH₂CH₃ | (CH₂)₈CH₃ |
| I-209 | CH₂CH₃ | CH₂CH₂CH₂CH₂CH₂CH₃ |

TABLE 1-continued

| | $R^1$ | $R^2$ |
|---|---|---|
| I-210 | $CH_2CH_3$ | $CH_2CH(CH_3)CH_2CH_2CH_3$ |
| I-211 | $CH_2CH_3$ | $CH_2CH_2CH_2CH_2CH_2CH_3$ |
| I-212 | $CH_2CH_3$ | $CH_2CH_2CH_2CH_2CH_2CH_2CH_2CH_3$ |
| I-213 | $CH_2CH_3$ | $CH_2CH_2CH(CH_3)CH_2C(CH_3)_3$ |
| I-214 | $CH_2CH_3$ | $CH_2CH_2C(CH_3)_2CH_2C(CH_3)_3$ |
| I-215 | $CH_2CH_3$ | $CH_2CH_2CH_2CH_2CH_2CH_3$ |
| I-216 | $CH_2CH_3$ | $CH_2CH(CH_3)CH_2CH_2CH_3$ |
| I-217 | $CH_2CH=CH_2$ | $CH_3$ |
| I-218 | $CH_2CH=CH_2$ | $CF_3$ |
| I-219 | $CH_2CH=CH_2$ | $CH_2CH_3$ |
| I-220 | $CH_2CH=CH_2$ | $CH_2CH_2CH_3$ |
| I-221 | $CH_2CH=CH_2$ | $CH_2OCH_3$ |
| I-222 | $CH_2CH=CH_2$ | $(CH_2)_3CH_3$ |
| I-223 | $CH_2CH=CH_2$ | $(CH_2)_4CH_3$ |
| I-224 | $CH_2CH=CH_2$ | $(CH_2)_5CH_3$ |
| I-225 | $CH_2CH=CH_2$ | $(CH_2)_6CH_3$ |
| I-226 | $CH_2CH=CH_2$ | $(CH_2)_7CH_3$ |
| I-227 | $CH_2CH=CH_2$ | $(CH_2)_8CH_3$ |

Examples of suitable nitriles of the formula II which may be mentioned are those compounds in which $R^1$ has one of the meanings given in any of rows I-1 to I-35. Examples of suitable nitriles of the formula II which may be mentioned are furthermore those compounds in which $R^1$ has one of the meanings given in rows I-93 to I-126, I-179, I-180 and I-217.

For the process according to the invention, it has furthermore been found to be advantageous for $R^3$ in formula III to be $C_1$-$C_8$-alkyl or $C_1$-$C_4$-alkoxy-$C_1$-$C_4$-alkyl. In particular, $R^3$ in formula III is $C_1$-$C_4$-alkyl, particularly preferably straight-chain $C_1$-$C_4$-alkyl and especially methyl or ethyl.

Examples of suitable carboxylic esters of the formula III are the compounds III-1 to III-30 listed in Table 2 in which $R^2$ and $R^3$ each have the meanings given in one row of the table:

TABLE 2

| | $R^2$ | $R^3$ |
|---|---|---|
| III-1 | $CH_3$ | $CH_3$ |
| III-2 | $C_2H_5$ | $CH_3$ |
| III-3 | $CF_3$ | $CH_3$ |
| III-4 | $CH_2$—$OCH_3$ | $CH_3$ |
| III-5 | $CH_2CH_2CH_3$ | $CH_3$ |
| III-6 | $(CH_2)_3CH_3$ | $CH_3$ |
| III-7 | $(CH_2)_4CH_3$ | $CH_3$ |
| III-8 | $(CH_2)_5CH_3$ | $CH_3$ |
| III-9 | $(CH_2)_6CH_3$ | $CH_3$ |
| III-10 | $(CH_2)_7CH_3$ | $CH_3$ |
| III-11 | $(CH_2)_8CH_3$ | $CH_3$ |
| III-12 | $CH_2CH(CH_3)CH_2CH_2CH_3$ | $CH_3$ |
| III-13 | $CH_2CH_2CH(CH_3)CH_2C(CH_3)_3$ | $CH_3$ |
| III-14 | $CH_2CH_2C(CH_3)_2CH_2C(CH_3)_3$ | $CH_3$ |
| III-15 | $CH_2CH(CH_3)CH_2CH_2CH_3$ | $CH_3$ |
| III-16 | $CH_3$ | $CH_2CH_3$ |
| III-17 | $C_2H_5$ | $CH_2CH_3$ |
| III-18 | $CF_3$ | $CH_2CH_3$ |
| III-19 | $CH_2$—$OCH_3$ | $CH_2CH_3$ |
| III-20 | $CH_2CH_2CH_3$ | $CH_2CH_3$ |
| III-21 | $(CH_2)_3CH_3$ | $CH_2CH_3$ |
| III-22 | $(CH_2)_4CH_3$ | $CH_2CH_3$ |
| III-23 | $(CH_2)_5CH_3$ | $CH_2CH_3$ |
| III-24 | $(CH_2)_6CH_3$ | $CH_2CH_3$ |
| III-25 | $(CH_2)_7CH_3$ | $CH_2CH_3$ |
| III-26 | $(CH_2)_8CH_3$ | $CH_2CH_3$ |
| III-27 | $CH_2CH(CH_3)CH_2CH_2CH_3$ | $CH_2CH_3$ |
| III-28 | $CH_2CH_2CH(CH_3)CH_2C(CH_3)_3$ | $CH_2CH_3$ |
| III-29 | $CH_2CH_2C(CH_3)_2CH_2C(CH_3)_3$ | $CH_2CH_3$ |
| III-30 | $CH_2CH(CH_3)CH_2CH_2CH_3$ | $CH_2CH_3$ |

In a particularly advantageous manner, the β-ketonitriles which can be obtained according to the invention can be employed for preparing 7-aminoazolopyrimidines of the general formula IV.

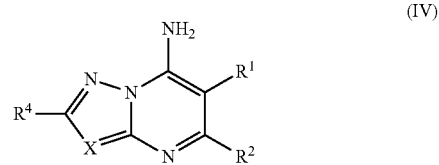

(IV)

In formula IV, $R^1$ and $R^2$ have the meanings mentioned above. $R^4$ is hydrogen, $NH_2$ or $C_1$-$C_6$-alkyl. X is N or a group C—$R^5$ in which $R^5$ is hydrogen or $C_1$-$C_6$-alkyl. According to a preferred embodiment of the invention, X is N. According to another preferred embodiment of the invention, X is CH.

The 7-aminoazolopyrimidines of the general formula IV can be prepared analogously to known processes of the prior art as described, for example, in EP-A 141317 and WO2006/087325, for example by reacting r-ketonitriles of the general formula I with an aminoazole compound of the formula V

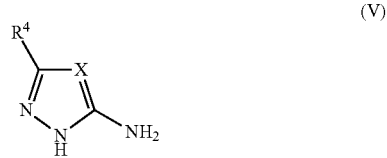

(V)

in which $R^4$ and X have the meanings mentioned above, or a tautomer of V.

Accordingly, the present invention also relates to a process for preparing 7-aminoazolopyrimidines of the general formula IV which comprises the following process steps:

a) Preparation of β-ketonitrile of the general formula I by the process described herein and b) reaction of the β-ketonitrile of the formula I with an aminoazole compound of the formula V or a tautomer thereof in a manner known per se, which gives the azolopyrimidine of the formula IV.

The reaction of the β-ketonitrile of the formula I with the aminoazole compound of the formula or its tautomer is preferably carried out in the presence of an acid. Suitable acids are, in principle, carboxylic acids, and also organic sulfonic acids. In the case of the sulfonic acids, catalytic amounts are typically employed, which are usually in the range of from 1 to 40 mol %, based on one mole of aminoazole of the formula V. In the case of the carboxylic acids, these carboxylic acids may also act as solvents.

Examples of suitable organic sulfonic acids are methanesulfonic acid, trifluoromethanesulfonic acid, benzenesulfonic acid, 2,3-dimethylbenzenesulfonic acid, 3,4-dimethylbenzenesulfonic acid and p-toluenesulfonic acid. Suitable organic carboxylic acids are formic acid, acetic acid, propionic acid, 2-methylpropionic acid, benzoic acid and mixtures thereof.

The reaction is preferably carried out in an organic inert solvent. Preference is given to those organic solvents in which the starting materials are at least partially or fully soluble. Examples of suitable solvents are in particular $C_1$-$C_4$-alkanols, such as methanol, ethanol, propanol, isopropanol, n-butanol, isobutanol, tert-butanol, the acyclic and alicyclic ethers mentioned above, aromatic hydrocarbons, in particular alkylaromatics as mentioned above, and also halogenated aromatics, for example chlorobenzene, dichlorobenzene, furthermore glycols and glycol monoalkyl ethers, diethylene glycol and their monoalkyl ethers, amides and lactams, in particular N,N-di-$C_1$-$C_4$-alkylamides of aliphatic carboxylic acids having 1 to 4 carbon atoms, such as dimethylformamide, diethylformamide, dibutylformamide, N,N-dimethylacetamide, the carboxylic acids mentioned above and mixtures of these solvents, and also mixtures of these solvents with water. In a preferred embodiment, the inert solvent consists to at least 80% by weight and in particular to at least 90% by weight of aromatic solvents, in particular alkylaromatics.

The reaction of IV with I is preferably carried out at temperatures in the range of from 80 to 250° C., in particular in the range of from 120 to 220° C. and especially in the range of from 150 to 190° C.

In the reaction, the water formed during the reaction is advantageously removed, if appropriate distilled off, for example as an azeotrope with the solvent used.

In a preferred embodiment of the invention, use is made of aminoazoles V in which X is N. In another likewise preferred embodiment, use is made of aminoazoles of the formula V in which X is CH. In the formulae IV and V, $R^4$ is preferably hydrogen.

Examples of preferred aminoazoles V are 3-amino-2H-1,2,4-triazole and its tautomers 3-amino-1H-1,2,4-triazole and 3-amino-4H-1,3,4-triazole, and also 3-amino-1H-pyrazole and its tautomer 3-amino-2H-pyrazole.

According to a preferred embodiment, step b) is carried out immediately after step a), without it being necessary to isolate the β-ketonitrile. In particular, for step b) of the process, a solution, obtained after neutralization of the potassium salt of the β-ketonitrile of the formula I formed in step a) of the β-ketonitrile I, in an inert organic solvent is used. This is in particular a solution in an inert solvent which consists to at least 80% by weight and in particular to at least 90% by weight of one or more alkylaromatics.

The reaction of the aminoazole IV or its tautomer can be carried out either batch-wise or else continuously. It is usually carried out batch-wise. To this end, the aminoazole IV and the β-ketonitrile are generally initially charged in a reaction vessel, if appropriate together with solvent and, if appropriate, acid, and the mixture is heated to reaction temperature. If appropriate, part of the solvent is distilled off together with the water of reaction formed. Suitable reaction vessels are the reactors mentioned for step a) which, if appropriate, may also be provided with means for distillative removal of solvents.

From the reaction mixture obtained in this manner, the compound IV can be isolated in a customary manner, for example by aqueous work-up, if appropriate followed by a crystallization for purification or by removal of the solvent and subsequent recrystallization of the product.

The examples below serve to illustrate the invention.

COMPARATIVE EXAMPLE 1

Example 10 of US2004/0171863

At room temperature, 10.88 g of sodium methoxide (0.20 mol), 41.70 g (0.60 mol) of n-butyronitrile and 30.14 g (0.43 mol) of n-butyl acetate were initially charged in a steel autoclave having a reaction volume of 250 ml. The autoclave was flushed with nitrogen, sealed and heated at 150° C. for two hours. The solid obtained after cooling was filtered off and dried. This gave 16.9 g of 3-cyanobutan-2-one in the form of its sodium salt (crude product).

16.7 g of the crude product were transferred into the reaction vessel. 20 ml of deionized water and 50 ml of ethyl acetate were added, and the mixture was stirred. The mixture was then acidified with a total of 11 ml of concentrated hydrochloric acid. Afterwards, the pH of the aqueous phase was pH 5. The organic phase was separated off and dried over magnesium sulfate. After filtration, the organic phase was concentrated to dryness using a rotary evaporator. This gave 9.00 g of a clear orange liquid which, according to gas chromatogram, consisted of 88.8% of 3-cyanopentanone. This corresponds to a total yield of 7.99 g or 27.7%, based on the n-butyl acetate employed.

COMPARATIVE EXAMPLE 2

7.34 g of sodium methoxide, 48.5 g of xylene, 64 g (0.40 mol) of decanenitrile and 17.9 g (0.17 mol) of ethyl propionate were initially charged in a steel autoclave having a reaction volume of 250 ml. The autoclave was flushed with nitrogen, sealed and then heated at 150° C. for two hours. The sodium salt obtained after cooling was filtered off and dried. In this manner, 38.8 g of dry crude product were obtained which were filled into a glass flask, and 27.00 g of deionized water and 60.84 g of ethyl acetate were added. The mixture was then acidified with 14.50 ml of concentrated hydrochloric acid. After the addition of hydrochloric acid, the pH of the aqueous phase was pH 4.5. The organic phase was separated off, dried over magnesium sulfate, filtered and then concentrated to dryness using a rotary evaporator. This gave 62.80 g of a crude product which, according to gas chromatogram, consisted of 78.2% unreacted nitrile and 11.27% of the desired product.

EXAMPLES ACCORDING TO THE INVENTION

Example 1

2-(2-Methoxyacetyl)decanonitrile

In a stirred vessel fitted with reflux condenser and dropping funnel, 199.96 g of solid potassium methoxide were initially charged, and 318 g of o-xylene were added. 15 g of ethanol were added, and the suspension was heated to reflux. A mixture of 170 g of decanonitrile and 180.8 g of ethyl methoxy acetate was then added via the dropping funnel over a period of 10 min. After the addition had ended, stirring was continued for 6 h, and the mixture was then cooled to 105° C. 373 g of water were then added, and the mixture was adjusted to pH 4 by addition of about 388 g of 20% strength hydrochloric acid. The temperature was set to 70° C., and the (lower) aqueous phase was removed. The organic phase was washed with another 186 g of water. After removal of the aqueous phase, the organic phase was concentrated to half of its original volume in order to remove the water. This gave 235.5 g of a pale yellow solution having a content of product of value of 62% a/a (GC), which can be reacted further as such. For purification, the compound was distilled under high vacuum, with the product passing over at 120 to 134° C./1 mbar.

$^1$H-NMR (CDCl$_3$): 0.89 (t, 3H); 1.2-1.55 (m, 12H); 1.88 (m, 2H); 3.45 (s, 3H), 3.75 (dd, 1H); 4.20 (s, 2H).

Example 2

2-Acetyldecanonitrile

In a stirred vessel fitted with reflux condenser and dropping funnel, 317 g of o-xylene were initially charged, 198.96 g of solid potassium methoxide were added and the mixture was heated at reflux. A mixture of 170 g of decanonitrile and 133.9 g of ethyl acetate was then added via the dropping funnel over a period of 10 min. After the addition had ended, stirring was continued for 4 h, and the mixture was then cooled to 105° C. 372 g of water were then added, and the mixture was adjusted to pH 4.3 by addition of about 470 g of 20% strength hydrochloric acid. The temperature was set to 65° C., and the (lower) aqueous phase was removed. The organic phase was washed with another 186 g of water. After removal of the aqueous phase, the organic phase was concentrated to about half of its original volume to remove the water. This gave 211.7 g of a light-yellow solution having a content of product of value of 66.8% a/a (GC), which solution can be reacted further as such. For purification, the compound was distilled under high vacuum, with the product passing over at 106 to 121° C./1 mbar.

$^1$H-NMR: 0.9 (t, 3H); 1.1-1.7 (m, 12H); 1.9 (m, 2H); 2.38 (s, 3H); 3.40 (dd, 1H).

Example 3

2-Propionylpent-4-enenitrile

In a 20 l jacketed reactor fitted with heating/cooling circuit and reflux condenser, 3500 g of potassium tert-butoxide were initially charged, and 6316 g of tetrahydrofuran was added. At a temperature of at most 10° C., a mixture of 1200 g of pentenenitrile and 1651 g of ethyl propionate was then pumped in over a period of 75 min. Stirring was continued at 8 to 10° C. for 3 h and then at 15° C. overnight. The mixture was then adjusted to pH of 3.8 by pumping in 6316 g of 20% strength hydrochloric acid, with the temperature increasing to 48° C. 2400 ml of water and 4000 ml of o-xylene were then added. The aqueous (lower) phase was then removed, and the organic phase was washed two more times with in each case 2400 ml of water. What remained were 14650 g of organic phase. Concentration on a rotary evaporator at 60° C. and 10 mbar gave 1873 g of an amber product having a content of 87.4% a/a (GC), which was reacted further as such.

$^1$H-NMR: 1.12 (s, 3H); 2.52 (q)+2.75 (m) (together 4H); 3.50 (t, 1H); 5.25 (m, 2H); 5.80 (m, 1H).

Example 4

2-Propionyldecanonitrile

In a stirred vessel fitted with reflux condenser and dropping funnel, 724 g of o-xylene were initially charged, 454.2 g of solid potassium methoxide were added and the mixture was heated at reflux. Initially 10% of a mixture of 392.0 g of decanonitrile and 360.6 g of ethyl propionate were then added via the dropping funnel over a period of 1 min, and the mixture was stirred for 15 min. The remainder of the mixture was then metered in over a period of 10 min. After the addition had ended, the mixture was stirred under gentle reflux for another 4 h and then cooled to 105° C. The mixture was discharged into 848 g of water in a second tank and adjusted to a pH of 6 by addition of about 1020 g of 20% strength hydrochloric acid. The temperature was set to 80° C., and the (lower) aqueous phase was removed. This gave 1316 g of a light-yellow solution having a content of product of value of 37.6% a/a (GC), which can be reacted further as such. For purification, the compound was distilled under high vacuum, with the product passing over at 130 to 140° C./1 mbar.

$^1$H-NMR: 0.9 (t, 3H); 1.11 (t, 3H), 1.2-1.4 (m, 10H); 1.4-1.55 (m, 2H); 1.8-2.0 (m, 2H); 2.75 (q, 2H), 3.40 (t, 1H).

General Procedure A for Preparing β-Ketonitriles of the General Formula I:

587 g (7.96 mol) of potassium methoxide, 940 g of ortho-xylene and 25 g of ethanol are initially charged in a reaction vessel provided with stirrer, reflux condenser and nitrogen inlet, and the mixture is then, under nitrogen, heated at reflux (bath temperature 150° C., internal temperature 132° C.). Via two separate feeds, over a period of 21 minutes, 3.23 mol of nitrile of the formula I and 4.4 mol of ester of the formula II are then added simultaneously to the reaction vessel, with the temperature being maintained. The mixture is then heated at reflux for a further four hours and subsequently cooled to 105° C. The hot content of the reaction flask is then discharged into a reaction tank containing 1190 g of water. The resulting mixture is stirred, then adjusted to pH 4-5 using 1350 g of 20% by weight strength aqueous hydrochloric acid and stirred for a further 15 min. Using 20% by weight strength hydrochloric acid, the aqueous phase is adjusted to pH 4 to 5, and then stirred for 15 minutes. The aqueous phase is then separated off, and the organic phase is washed with a total of 1100 g of deionized water. Using a rotary evaporator, the organic phase is then concentrated to about 75% of its original volume.

For purification of the compound, the solvent is initially distilled off under reduced pressure. The residue that remained is then rectified under high vacuum. This gives the compounds of the formula I as main fraction in the form of colorless to pale yellow oils. The unreacted part of the starting material is obtained as prefractions suitable for recycling.

In this manner, it is possible to prepare the following compounds of the formula I, unless indicated otherwise:

| Ex. | R$^1$ | R$^2$ | Yield [%]$^{1)}$ |
|---|---|---|---|
| 1 | CH$_2$CH$_2$CH$_2$CH$_2$CH$_2$CH$_2$CH$_2$CH$_3$ | CH$_2$OCH$_3$ | 59.2 |
| 2 | CH$_2$CH$_2$CH$_2$CH$_2$CH$_2$CH$_2$CH$_3$ | CH$_3$ | 66.1 |
| 3 | CH$_2$CH=CH$_2$ | CH$_2$CH$_3$ | 81.0 |
| 4 | CH$_2$CH$_2$CH$_2$CH$_2$CH$_2$CH$_2$CH$_2$CH$_3$ | CH$_2$CH$_3$ | 92.0 |

-continued

| Ex. | R¹ | R² | Yield [%][1] |
|---|---|---|---|
| 5 | CH₂CH₂CH(CH₃)CH₂C(CH₃)₃ | CH₃ | |
| 6 | CH₂CH₂C(CH₃)₂CH₂C(CH₃)₃ | CH₃ | |
| 7 | CH₂CH₂CH₂CH₂CH₂CH₃ | CF₃ | |
| 8 | CH₂CH(CH₃)CH₂CH₂CH₃ | CF₃ | |
| 9 | CH₂CH₂CH₂CH₂CH₂CH₂CH₃ | CF₃ | |
| 10 | CH₂CH₂CH₂CH₂CH₂CH₂CH₂CH₃ | CF₃ | |
| 11 | CH₂CH₂CH(CH₃)CH₂C(CH₃)₃ | CF₃ | |
| 12 | CH₂CH₂C(CH₃)₂CH₂C(CH₃)₃ | CF₃ | |
| 13 | CH₂CH₂CH₂CH₂CH₂CH₃ | CH₂CH₃ | |
| 14 | CH₂CH(CH₃)CH₂CH₂CH₃ | CH₂CH₃ | |
| 15 | CH₂CH₂CH₂CH₂CH₂CH₂CH₃ | CH₂CH₃ | |
| 16 | CH₂CH₂CH₂CH₂CH₂CH₂CH₂CH₃ | CH₃ | |
| 17 | CH₂CH₂CH(CH₃)CH₂C(CH₃)₃ | CH₂CH₃ | |
| 18 | CH₂CH₂C(CH₃)₂CH₂C(CH₃)₃ | CH₂CH₃ | |
| 19 | CH₂CH₂CH₂CH₂CH₂CH₃ | CH₂CH₂CH₃ | |
| 20 | CH₂CH(CH₃)CH₂CH₂CH₃ | CH₂CH₂CH₃ | |
| 21 | CH₂CH₂CH₂CH₂CH₂CH₂CH₃ | CH₂CH₂CH₃ | |
| 22 | CH₂CH₂CH₂CH₂CH₂CH₂CH₂CH₃ | CH₂CH₂CH₃ | |
| 23 | CH₂CH₂CH(CH₃)CH₂C(CH₃)₃ | CH₂CH₂CH₃ | |
| 24 | CH₂CH₂C(CH₃)₂CH₂C(CH₃)₃ | CH₂CH₂CH₃ | |
| 25 | CH₂CH₂CH₂CH₂CH₂CH₃ | CH₂OCH₃ | |
| 26 | CH₂CH(CH₃)CH₂CH₂CH₃ | CH₂OCH₃ | |
| 27 | CH₂CH₂CH₂CH₂CH₂CH₂CH₃ | CH₂OCH₃ | |
| 28 | CH₂CH₂CH₂CH₂CH₂CH₃ | CH₃ | |
| 29 | CH₂CH₂CH(CH₃)CH₂C(CH₃)₃ | CH₂OCH₃ | |
| 30 | CH₂CH₂C(CH₃)₂CH₂C(CH₃)₃ | CH₂OCH₃ | |
| 31 | CH₂CH₃ | CH₂CH₂CH₂CH₂CH₂CH₃ | |
| 32 | CH₂CH₃ | CH₂CH(CH₃)CH₂CH₂CH₃ | |
| 33 | CH₂CH₃ | CH₂CH₂CH₂CH₂CH₂CH₂CH₃ | |
| 34 | CH₂CH₃ | CH₂CH₂CH₂CH₂CH₂CH₂CH₂CH₃ | |
| 35 | CH₂CH₃ | CH₂CH₂CH(CH₃)CH₂C(CH₃)₃ | |
| 36 | CH₂CH₃ | CH₂CH₂C(CH₃)₂CH₂C(CH₃)₃ | |
| 37 | CH₂CH=CH₂ | CH₃ | |
| 38 | CH₂CH=CH₂ | CF₃ | |
| 39 | CH₂CH(CH₃)CH₂CH₂CH₃ | CH₃ | |
| 40 | CH₂CH=CH₂ | CH₂CH₃ | |
| 41 | CH₂CH=CH₂ | CH₂OCH₃ | |
| 42 | CH₂CH=CH₂ | (CH₂)₃CH₃ | |
| 43 | CH₂CH=CH₂ | (CH₂)₄CH₃ | |
| 44 | CH₂CH=CH₂ | (CH₂)₅CH₃ | |
| 45 | CH₂CH=CH₂ | (CH₂)₆CH₃ | |
| 46 | CH₂CH=CH₂ | (CH₂)₇CH₃ | |
| 47 | CH₂CH=CH₂ | (CH₂)₈CH₃ | |

[1] based on the nitrile II

Example 48

5-Ethyl-6-octyl-[1,2,4]triazolo[1,5-a]pyrimidin-7-ylamine

In a 2.5 l jacketed vessel fitted with condenser and water separator, 737 g of o-xylene was initially charged, and 39.5 g of chlorosulfonic acid was added. 191.2 g of 3-amino-1,2,4-triazole and 1254 g of a solution of 2-propionyldecanonitrile (37.7% by weight in o-xylene) were added, and the mixture was heated to reflux. The mixture was stirred under reflux for 12 hours, and the water of reaction formed was removed via a phase separator. Once no more water was separated off, the mixture was cooled to 140° C. and 59.4 g of triethylamine were added. On further cooling, the product precipitated in the form of colorless crystals. At a temperature 105° C., 152.8 g of methanol were added. The mixture was cooled further to 20° C., and the solid formed was separated off. The filtercake was washed with a mixture of 850 g of methanol and 119 g of water and then dried under reduced pressure. This gave 525.5 g of colorless crystals having a content of 98.3% a/a (HPLC). The title compound was obtained as a mixture of two modifications having melting points of 199° C. and 201° C., respectively. Yield: 83.0%.

Example 49

6-Allyl-5-ethyl-[1,2,4]triazolo[1,5-a]pyrimidin-7-ylamine

In a 20 l jacketed vessel fitted with reflux condenser and water separator, 14650 g of o-xylene were initially charged, and 411 g of chlorosulfonic acid were added. 2074 g of 3-amino-1,2,4-triazole and 3690 g of a solution of 2-propionylpent-4-enenitrile (87.4% in o-xylene) were added, and the mixture was heated to reflux. The mixture was stirred under reflux for 14 hours, and the water of reaction formed was removed via a phase separator. Once no more water separated off, the mixture was cooled to 130° C. and 634 g of triethylamine were added. On further cooling, the product precipitated in the form of colorless crystals. At a temperature of 100° C., 2350 g of isopropanol were added. The mixture was cooled further to 20° C., and the solid formed was separated off. The filtercake was washed with 1500 ml of a 1:1 mixture of isopropanol and water and then dried under reduced pressure. This gives 4057 g of a colorless powder. Melting point: 258° C. (decomposition), $^1$H-NMR: 1.35 (t, 3H); 2.88 (q, 2H); 3.45 (d, 2H); 5.09 (d, 2H); 5.20 (d, 2H); 5.6 (s, broad, 2H); 5.8-6.0 (m, 1H); 8.30 (s, 1H). Yield: 84.0%.

Example 50

Analogously to Example 48, 5-methoxymethyl-6-octyl-[1,2,4]triazolo[1,5-a]pyrimidin-7-ylamine was prepared from 2-(2-methoxyacetyl)decanonitrile. This gave colorless crystals having a melting point of from 181 to 182° C. Yield: 85.1%.

Example 51

Analogously to Example 48, 5-methyl-6-octyl-[1,2,4]triazolo[1,5-a]pyrimidin-7-ylamine was prepared from 2-acetyldecanonitrile. This gave colorless crystals. The title compound was obtained as a mixture of two modifications having melting points of 199 to 200° C. and 216 to 217° C., respectively. Yield: 79.2%.

General Procedure B for Preparing 7-Aminoazolopyrimidines of the General Formula IV Variant 1:

A solution of 97 mmol of a ketonitrile according to procedure A is dissolved in 60 ml of mesitylene and, together with 8.1 g (97 mmol) of 3-amino-1,2,4-triazole (or 97 mmol of 3-aminopyrazole) and 3.8 g of 4-toluenesulfonic acid, heated at 180° C. for three hours, during which a little solvent and the reaction water distils off. The solvent is then distilled off completely, and the residue is taken up in methylene chloride. After washing with saturated aqueous $NaHCO_3$ solution and water, the organic phase is dried, the solvent is removed and the residue is digested with diethyl ether. The compounds of the formula IV remain as colorless to pale yellow crystals or as colorless to pale yellow oils.

Variant 2:

At room temperature, oleum (18.4 mmol $SO_3$) is added to 60 ml of o-xylene, and the mixture is then heated at reflux together with 97 mmol of a ketonitrile according to procedure A, 8.1 g (97 mmol) of 3-amino-1,2,4-triazole (or 97 mmol of 3-amino-pyrazole) and 3.8 g of 4-toluenesulfonic acid for eight hours, and during this time, the water of reaction is removed. The solvent is then distilled off completely, and the residue is taken up in methylene chloride. After washing with saturated $NaHCO_3$ solution and water, the organic phase is dried and freed from the solvent and the residue is digested with diethyl ether. The compounds of the formula IV are obtained as colorless to pale yellow crystals or as colorless to pale yellow oils.

Variant 3:

At room temperature, 2.14 g (18.4 mmol) of chlorosulfonic acid are added to 60 ml of o-xylene, and the mixture is then heated at reflux together with 97 mmol of a ketonitrile according to procedure A, 8.1 g (97 mmol) of 3-amino-1,2,4-triazole (or 97 mmol of 3-aminopyrazole) and 3.8 g of 4-toluenesulfonic acid for ten hours, and the water of reaction formed is removed. The mixture is then cooled to 20° C. over a period of 10 h. The suspension formed is filtered off, and the filtercake is then washed with methanol and water. After drying under reduced pressure, the compounds of the formula IV are obtained as colorless to pale yellow crystals or as colorless to pale yellow oils.

In this manner, it is possible to prepare the following compounds of the formula IV, unless indicated otherwise:

| Ex. | $R^1$ | $R^2$ | X | $R^4$ |
|---|---|---|---|---|
| 52 | $CH_2CH_2CH_2CH_2CH_2CH_3$ | $CH_3$ | N | H |
| 53 | $CH_2CH(CH_3)CH_2CH_2CH_3$ | $CH_3$ | N | H |
| 54 | $CH_2CH_2CH_2CH_2CH_2CH_2CH_3$ | $CH_3$ | N | H |
| 55 | $CH_2CH_2CH(CH_3)CH_2C(CH_3)_3$ | $CH_3$ | N | H |
| 56 | $CH_2CH_2C(CH_3)_2CH_2C(CH_3)_3$ | $CH_3$ | N | H |
| 57 | $CH_2CH_2CH_2CH_2CH_2CH_3$ | $CF_3$ | N | H |
| 58 | $CH_2CH(CH_3)CH_2CH_2CH_3$ | $CF_3$ | N | H |
| 59 | $CH_2CH_2CH_2CH_2CH_2CH_2CH_3$ | $CF_3$ | N | H |
| 60 | $CH_2CH_2CH_2CH_2CH_2CH_2CH_2CH_3$ | $CF_3$ | N | H |
| 61 | $CH_2CH_2CH(CH_3)CH_2C(CH_3)_3$ | $CF_3$ | N | H |
| 62 | $CH_2CH_2C(CH_3)_2CH_2C(CH_3)_3$ | $CF_3$ | N | H |
| 63 | $CH_2CH_2CH_2CH_2CH_2CH_3$ | $CH_2CH_3$ | N | H |
| 64 | $CH_2CH(CH_3)CH_2CH_2CH_3$ | $CH_2CH_3$ | N | H |
| 65 | $CH_2CH_2CH_2CH_2CH_2CH_2CH_3$ | $CH_2CH_3$ | N | H |
| 66 | $CH_2CH_2CH(CH_3)CH_2C(CH_3)_3$ | $CH_2CH_3$ | N | H |
| 67 | $CH_2CH_2C(CH_3)_2CH_2C(CH_3)_3$ | $CH_2CH_3$ | N | H |
| 68 | $CH_2CH_2CH_2CH_2CH_2CH_3$ | $CH_2CH_2CH_3$ | N | H |
| 69 | $CH_2CH(CH_3)CH_2CH_2CH_3$ | $CH_2CH_2CH_3$ | N | H |
| 70 | $CH_2CH_2CH_2CH_2CH_2CH_2CH_3$ | $CH_2CH_2CH_3$ | N | H |
| 71 | $CH_2CH_2CH_2CH_2CH_2CH_2CH_2CH_3$ | $CH_2CH_2CH_3$ | N | H |
| 72 | $CH_2CH_2CH(CH_3)CH_2C(CH_3)_3$ | $CH_2CH_2CH_3$ | N | H |
| 73 | $CH_2CH_2C(CH_3)_2CH_2C(CH_3)_3$ | $CH_2CH_2CH_3$ | N | H |
| 74 | $CH_2CH_2CH_2CH_2CH_2CH_3$ | $CH_2OCH_3$ | N | H |
| 75 | $CH_2CH(CH_3)CH_2CH_2CH_3$ | $CH_2OCH_3$ | N | H |
| 76 | $CH_2CH_2CH_2CH_2CH_2CH_2CH_3$ | $CH_2OCH_3$ | N | H |
| 77 | $CH_2CH_2CH(CH_3)CH_2C(CH_3)_3$ | $CH_2OCH_3$ | N | H |
| 78 | $CH_2CH_2C(CH_3)_2CH_2C(CH_3)_3$ | $CH_2OCH_3$ | N | H |
| 79 | $CH_2CH_2CH_2CH_2CH_2CH_3$ | $CH_3$ | N | $NH_2$ |
| 80 | $CH_2CH(CH_3)CH_2CH_2CH_3$ | $CH_3$ | N | $NH_2$ |
| 81 | $CH_2CH_2CH_2CH_2CH_2CH_2CH_3$ | $CH_3$ | N | $NH_2$ |
| 82 | $CH_2CH_2CH_2CH_2CH_2CH_2CH_2CH_3$ | $CH_3$ | N | $NH_2$ |
| 83 | $CH_2CH_2CH(CH_3)CH_2C(CH_3)_3$ | $CH_3$ | N | $NH_2$ |
| 84 | $CH_2CH_2C(CH_3)_2CH_2C(CH_3)_3$ | $CH_3$ | N | $NH_2$ |
| 85 | $CH_2CH_2CH_2CH_2CH_2CH_3$ | $CF_3$ | N | $NH_2$ |
| 86 | $CH_2CH(CH_3)CH_2CH_2CH_3$ | $CF_3$ | N | $NH_2$ |
| 87 | $CH_2CH_2CH_2CH_2CH_2CH_2CH_3$ | $CF_3$ | N | $NH_2$ |
| 88 | $CH_2CH_2CH_2CH_2CH_2CH_2CH_2CH_3$ | $CF_3$ | N | $NH_2$ |
| 89 | $CH_2CH_2CH(CH_3)CH_2C(CH_3)_3$ | $CF_3$ | N | $NH_2$ |
| 90 | $CH_2CH_2C(CH_3)_2CH_2C(CH_3)_3$ | $CF_3$ | N | $NH_2$ |
| 91 | $CH_2CH_2CH_2CH_2CH_2CH_3$ | $CH_2CH_3$ | N | $NH_2$ |
| 92 | $CH_2CH(CH_3)CH_2CH_2CH_3$ | $CH_2CH_3$ | N | $NH_2$ |
| 93 | $CH_2CH_2CH_2CH_2CH_2CH_2CH_3$ | $CH_2CH_3$ | N | $NH_2$ |
| 94 | $CH_2CH_2CH_2CH_2CH_2CH_2CH_2CH_3$ | $CH_2CH_3$ | N | $NH_2$ |
| 95 | $CH_2CH_2CH(CH_3)CH_2C(CH_3)_3$ | $CH_2CH_3$ | N | $NH_2$ |
| 96 | $CH_2CH_2C(CH_3)_2CH_2C(CH_3)_3$ | $CH_2CH_3$ | N | $NH_2$ |
| 97 | $CH_2CH_2CH_2CH_2CH_2CH_3$ | $CH_2CH_2CH_3$ | N | $NH_2$ |
| 98 | $CH_2CH(CH_3)CH_2CH_2CH_3$ | $CH_2CH_2CH_3$ | N | $NH_2$ |
| 99 | $CH_2CH_2CH_2CH_2CH_2CH_2CH_3$ | $CH_2CH_2CH_3$ | N | $NH_2$ |
| 100 | $CH_2CH_2CH_2CH_2CH_2CH_2CH_2CH_3$ | $CH_2CH_2CH_3$ | N | $NH_2$ |
| 101 | $CH_2CH_2CH(CH_3)CH_2C(CH_3)_3$ | $CH_2CH_2CH_3$ | N | $NH_2$ |
| 102 | $CH_2CH_2C(CH_3)_2CH_2C(CH_3)_3$ | $CH_2CH_2CH_3$ | N | $NH_2$ |
| 103 | $CH_2CH_2CH_2CH_2CH_2CH_3$ | $CH_2OCH_3$ | N | $NH_2$ |
| 104 | $CH_2CH(CH_3)CH_2CH_2CH_3$ | $CH_2OCH_3$ | N | $NH_2$ |
| 105 | $CH_2CH_2CH_2CH_2CH_2CH_2CH_3$ | $CH_2OCH_3$ | N | $NH_2$ |
| 106 | $CH_2CH_2CH_2CH_2CH_2CH_2CH_2CH_3$ | $CH_2OCH_3$ | N | $NH_2$ |
| 107 | $CH_2CH_2CH(CH_3)CH_2C(CH_3)_3$ | $CH_2OCH_3$ | N | $NH_2$ |
| 108 | $CH_2CH_2C(CH_3)_2CH_2C(CH_3)_3$ | $CH_2OCH_3$ | N | $NH_2$ |
| 109 | $CH_2CH_2CH_2CH_2CH_2CH_3$ | $CH_3$ | CH | H |
| 110 | $CH_2CH(CH_3)CH_2CH_2CH_3$ | $CH_3$ | CH | H |
| 111 | $CH_2CH_2CH_2CH_2CH_2CH_2CH_3$ | $CH_3$ | CH | H |
| 112 | $CH_2CH_2CH_2CH_2CH_2CH_2CH_2CH_3$ | $CH_3$ | CH | H |
| 113 | $CH_2CH_2CH(CH_3)CH_2C(CH_3)_3$ | $CH_3$ | CH | H |
| 114 | $CH_2CH_2C(CH_3)_2CH_2C(CH_3)_3$ | $CH_3$ | CH | H |
| 115 | $CH_2CH_2CH_2CH_2CH_2CH_3$ | $CF_3$ | CH | H |
| 116 | $CH_2CH(CH_3)CH_2CH_2CH_3$ | $CF_3$ | CH | H |
| 117 | $CH_2CH_2CH_2CH_2CH_2CH_2CH_3$ | $CF_3$ | CH | H |
| 118 | $CH_2CH_2CH_2CH_2CH_2CH_2CH_2CH_3$ | $CF_3$ | CH | H |
| 119 | $CH_2CH_2CH(CH_3)CH_2C(CH_3)_3$ | $CF_3$ | CH | H |
| 120 | $CH_2CH_2C(CH_3)_2CH_2C(CH_3)_3$ | $CF_3$ | CH | H |
| 121 | $CH_2CH_2CH_2CH_2CH_2CH_3$ | $CH_2CH_3$ | CH | H |
| 122 | $CH_2CH(CH_3)CH_2CH_2CH_3$ | $CH_2CH_3$ | CH | H |
| 123 | $CH_2CH_2CH_2CH_2CH_2CH_2CH_3$ | $CH_2CH_3$ | CH | H |
| 124 | $CH_2CH_2CH_2CH_2CH_2CH_2CH_2CH_3$ | $CH_2CH_3$ | CH | H |
| 125 | $CH_2CH_2CH(CH_3)CH_2C(CH_3)_3$ | $CH_2CH_3$ | CH | H |
| 126 | $CH_2CH_2C(CH_3)_2CH_2C(CH_3)_3$ | $CH_2CH_3$ | CH | H |
| 127 | $CH_2CH_2CH_2CH_2CH_2CH_3$ | $CH_2CH_2CH_3$ | CH | H |
| 128 | $CH_2CH(CH_3)CH_2CH_2CH_3$ | $CH_2CH_2CH_3$ | CH | H |
| 129 | $CH_2CH_2CH_2CH_2CH_2CH_2CH_3$ | $CH_2CH_2CH_3$ | CH | H |
| 130 | $CH_2CH_2CH_2CH_2CH_2CH_2CH_2CH_3$ | $CH_2CH_2CH_3$ | CH | H |
| 131 | $CH_2CH_2CH(CH_3)CH_2C(CH_3)_3$ | $CH_2CH_2CH_3$ | CH | H |

-continued

| Ex. | R¹ | R² | X | R⁴ |
|---|---|---|---|---|
| 132 | $CH_2CH_2C(CH_3)_2CH_2C(CH_3)_3$ | $CH_2CH_2CH_3$ | CH | H |
| 133 | $CH_2CH_2CH_2CH_2CH_3$ | $CH_2OCH_3$ | CH | H |
| 134 | $CH_2CH(CH_3)CH_2CH_2CH_3$ | $CH_2OCH_3$ | CH | H |
| 135 | $CH_2CH_2CH_2CH_2CH_2CH_3$ | $CH_2OCH_3$ | CH | H |
| 136 | $CH_2CH_2CH_2CH_2CH_2CH_2CH_3$ | $CH_2OCH_3$ | CH | H |
| 137 | $CH_2CH_2CH(CH_3)CH_2C(CH_3)_3$ | $CH_2OCH_3$ | CH | H |
| 138 | $CH_2CH_2C(CH_3)_2CH_2C(CH_3)_3$ | $CH_2OCH_3$ | CH | H |
| 139 | $CH_2CH=CH_2$ | $CH_3$ | N | H |
| 140 | $CH_2CH=CH_2$ | $CF_3$ | N | H |
| 141 | $CH_2CH=CH_2$ | $CH_2CH_2CH_3$ | N | H |
| 142 | $CH_2CH=CH_2$ | $CH_2OCH_3$ | N | H |
| 143 | $CH_2CH=CH_2$ | $(CH_2)_3CH_3$ | N | H |
| 144 | $CH_2CH=CH_2$ | $(CH_2)_4CH_3$ | N | H |
| 145 | $CH_2CH=CH_2$ | $(CH_2)_5CH_3$ | N | H |
| 146 | $CH_2CH=CH_2$ | $(CH_2)_6CH_3$ | N | H |
| 147 | $CH_2CH=CH_2$ | $(CH_2)_7CH_3$ | N | H |
| 148 | $CH_2CH=CH_2$ | $(CH_2)_8CH_3$ | N | H |
| 149 | $CH_2CH=CH_2$ | $CH_3$ | CH | H |
| 150 | $CH_2CH=CH_2$ | $CF_3$ | CH | H |
| 151 | $CH_2CH=CH_2$ | $CH_2CH_3$ | CH | H |
| 152 | $CH_2CH=CH_2$ | $CH_2CH_2CH_3$ | CH | H |
| 153 | $CH_2CH=CH_2$ | $CH_2OCH_3$ | CH | H |
| 154 | $CH_2CH=CH_2$ | $(CH_2)_3CH_3$ | CH | H |
| 155 | $CH_2CH=CH_2$ | $(CH_2)_4CH_3$ | CH | H |
| 156 | $CH_2CH=CH_2$ | $(CH_2)_5CH_3$ | CH | H |
| 157 | $CH_2CH=CH_2$ | $(CH_2)_6CH_3$ | CH | H |
| 158 | $CH_2CH=CH_2$ | $(CH_2)_7CH_3$ | CH | H |
| 159 | $CH_2CH=CH_2$ | $(CH_2)_8CH_3$ | CH | H |

[2)] based on the ketonitrile of the formula I

The invention claimed is:

1. A process for preparing a compound of the formula IV

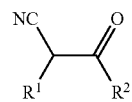

in which $R^1$ is $C_2$-$C_{12}$-alkyl, $C_2$-$C_{12}$-alkenyl, $C_2$-$C_{12}$-alkynyl, $C_3$-$C_8$-cycloalkyl, $C_3$-$C_8$-cycloalkyl-$C_1$-$C_4$-alkyl, phenyl-$C_1$-$C_4$-alkyl, phenoxy-$C_1$-$C_4$-alkyl or benzyloxy-$C_1$-$C_4$-alkyl, where $C_2$-$C_{12}$-alkyl may be substituted by one of the radicals $R^A$, the $C_3$-$C_8$-cycloalkyl groups in the radicals mentioned above may be substituted by 1, 2, 3, 4 or 5 radicals $R^B$ and the phenyl groups in the radicals mentioned above may be substituted by 1, 2, 3, 4 or 5 radicals $R^C$;

$R^A$ is selected from the group consisting of $C_1$-$C_{10}$-alkoxy, $C_1$-$C_6$-alkoxy-$C_1$-$C_4$-alkoxy, $C_1$-$C_{10}$-alkylthio, $NH_2$, $C_1$-$C_{10}$-alkylamino and di-$C_1$-$C_{10}$-alkylamino;

$R^B$ is selected from the group consisting of fluorine, $C_1$-$C_4$-alkyl, $C_1$-$C_4$-perfluoroalkyl and the meanings given for $R^A$;

$R^C$ is selected from the group consisting of fluorine, nitro, $C_1$-$C_4$-alkyl, $C_1$-$C_4$-perfluoralkyl and the meanings given for $R^A$, where $R^1$ has at least 3 carbon atoms $R^2$ is $C_1$-$C_8$-alkyl;

$R^4$ is hydrogen, $NH_2$ or $C_1$-$C_6$-alkyl and

X is N or a group C—$R^5$, where $R^5$ is hydrogen or $C_1$-$C_6$-alkyl;

which comprises:

a) preparing a compound of general formula I

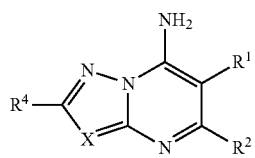

in which $R^1$ and $R^2$ have one of the meanings mentioned above, and b) reacting the compound of general formula (I) with a compound of the formula V

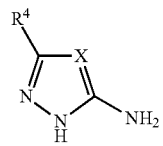

or a tautomer thereof, in a known manner, giving the compound of the formula IV.

2. The process as claimed in claim 1 where the reaction mixture obtained in step a), which comprises the compound of the formula II, is neutralized and, without further purification, reacted in step b) with the compound of the formula V.

* * * * *

UNITED STATES PATENT AND TRADEMARK OFFICE
CERTIFICATE OF CORRECTION

PATENT NO. : 8,501,748 B2
APPLICATION NO. : 13/616883
DATED : August 6, 2013
INVENTOR(S) : Vogelbacher et al.

Page 1 of 1

It is certified that error appears in the above-identified patent and that said Letters Patent is hereby corrected as shown below:

Title Page, (62) Related U.S. Application Data, after "application No. 12/528,700,", replace "filed as application" with the following:

--filed August 26, 2009, which is a national stage application of International Application--

Signed and Sealed this
Twenty-second Day of October, 2013

Teresa Stanek Rea
*Deputy Director of the United States Patent and Trademark Office*